United States Patent
McGoldrick et al.

(10) Patent No.: US 10,206,668 B2
(45) Date of Patent: Feb. 19, 2019

(54) IMPLANTABLE SEALABLE MEMBER WITH MESH LAYER

(71) Applicant: Vivasure Medical Limited, Galway (IE)

(72) Inventors: Mark McGoldrick, Athlone (IE); Bartosz Pawlikowski, Moycullen (IE); Peter Grant, Dangan (IE); Noelle Barrett, Knocknacarra (IE); Gerard Brett, Claregalway (IE); Christopher Martin, Oughterard (IE)

(73) Assignee: Vivasure Medical Limited, Galway (IE)

( * ) Notice: Subject to any disclaimer, the term of this patent is extended or adjusted under 35 U.S.C. 154(b) by 0 days.

(21) Appl. No.: 15/459,502

(22) Filed: Mar. 15, 2017

(65) Prior Publication Data
US 2017/0181736 A1    Jun. 29, 2017

Related U.S. Application Data

(63) Continuation of application No. 14/970,284, filed on Dec. 15, 2015.
(Continued)

(51) Int. Cl.
*A61B 17/00* (2006.01)
*B05D 1/04* (2006.01)
(Continued)

(52) U.S. Cl.
CPC .......... *A61B 17/0057* (2013.01); *B05D 1/007* (2013.01); *B05D 1/04* (2013.01);
(Continued)

(58) Field of Classification Search
CPC ............ A61F 2/0063; A61F 2210/0014; A61F 2210/0057; A61F 2220/0016; A61F 2230/0006
See application file for complete search history.

(56) References Cited

U.S. PATENT DOCUMENTS

| | | |
|---|---|---|
| 321,721 A | 7/1885 | Hassan |
| 2,001,638 A | 5/1935 | Tornsjo |
| (Continued) | | |

FOREIGN PATENT DOCUMENTS

| | | |
|---|---|---|
| DE | 102010048908 A1 | 4/2012 |
| EP | 0761250 A1 | 3/1997 |
| (Continued) | | |

OTHER PUBLICATIONS

U.S. Appl. No. 62/092,235, filed Dec. 15, 2014, Grant et al.
(Continued)

*Primary Examiner* — Julie A Szpira
(74) *Attorney, Agent, or Firm* — William R. Haulbrook; Choate, Hall & Stewart LLP

(57) ABSTRACT

The provided technologies provide an implant closure device having a mesh layer formed on a flexible substrate, collectively forming a sealable member, that improves a seal formed over an aperture in a body lumen. The mesh facilitates a faster and more secure adherence of the sealable member to the surrounding edges at the puncture site. Furthermore, the provided technology may promote platelet-capture and encourage localized platelet aggregation at the exposed collagen in the wound edges on the mesh layer. The platelet impregnated mesh layer can facilitate cellular adhesion, enabling the sealable member that is local to the wound opening to act, in essence, as a "biological glue".

23 Claims, 13 Drawing Sheets

Related U.S. Application Data

(60) Provisional application No. 62/092,212, filed on Dec. 15, 2014.

(51) Int. Cl.
  *B05D 3/00* (2006.01)
  *B05D 1/00* (2006.01)
  *B05D 7/04* (2006.01)

(52) U.S. Cl.
  CPC .............. *B05D 3/002* (2013.01); *B05D 7/04* (2013.01); *A61B 2017/00004* (2013.01); *A61B 2017/0061* (2013.01); *A61B 2017/00526* (2013.01); *A61B 2017/00575* (2013.01); *A61B 2017/00592* (2013.01); *A61B 2017/00597* (2013.01); *A61B 2017/00615* (2013.01); *A61B 2017/00623* (2013.01); *A61B 2017/00676* (2013.01); *A61B 2017/00862* (2013.01)

(56) References Cited

U.S. PATENT DOCUMENTS

| | | |
|---|---|---|
| 2,560,162 A | 7/1951 | Ferguson |
| 2,778,254 A | 1/1957 | Carapellotti |
| 3,874,388 A | 4/1975 | King et al. |
| 4,299,230 A | 11/1981 | Kubota |
| 4,583,540 A | 4/1986 | Malmin |
| 4,650,472 A | 3/1987 | Bates |
| 4,705,040 A | 11/1987 | Mueller et al. |
| 4,744,364 A | 5/1988 | Kensey |
| 4,852,568 A | 8/1989 | Kensey |
| 4,890,612 A | 1/1990 | Kensey |
| 4,896,668 A | 1/1990 | Popoff et al. |
| 5,021,059 A | 6/1991 | Kensey et al. |
| 5,037,433 A | 8/1991 | Wilk et al. |
| 5,053,046 A | 10/1991 | Janese |
| 5,085,661 A | 2/1992 | Moss |
| 5,127,412 A | 7/1992 | Cosmetto et al. |
| 5,171,258 A | 12/1992 | Bales et al. |
| 5,192,301 A | 3/1993 | Kamiya et al. |
| 5,269,804 A | 12/1993 | Bales et al. |
| 5,282,827 A | 2/1994 | Kensey et al. |
| 5,320,461 A | 6/1994 | Stanesic |
| 5,330,488 A | 7/1994 | Goldrath |
| 5,336,231 A | 8/1994 | Adair |
| 5,342,393 A | 8/1994 | Stack |
| 5,350,399 A | 9/1994 | Erlebacher et al. |
| 5,366,480 A | 11/1994 | Corriveau et al. |
| 5,391,182 A | 2/1995 | Chin |
| 5,431,639 A | 7/1995 | Shaw |
| 5,462,560 A | 10/1995 | Stevens |
| 5,470,337 A | 11/1995 | Moss |
| 5,501,691 A | 3/1996 | Goldrath |
| 5,501,700 A | 3/1996 | Hirata |
| 5,507,755 A | 4/1996 | Gresl et al. |
| 5,527,322 A | 6/1996 | Klein et al. |
| 5,531,759 A | 7/1996 | Kensey et al. |
| 5,545,178 A | 8/1996 | Kensey et al. |
| 5,549,633 A | 8/1996 | Evans et al. |
| 5,593,422 A | 1/1997 | Muijs Van de Moer et al. |
| 5,601,557 A | 2/1997 | Hayhurst |
| 5,601,571 A | 2/1997 | Moss |
| 5,620,461 A | 4/1997 | Muijs Van De Moer et al. |
| 5,653,716 A | 8/1997 | Malo et al. |
| 5,662,681 A | 9/1997 | Nash et al. |
| 5,665,096 A | 9/1997 | Yoon |
| 5,676,689 A | 10/1997 | Kensey et al. |
| 5,690,674 A | 11/1997 | Diaz |
| 5,700,273 A | 12/1997 | Buelna et al. |
| 5,700,277 A | 12/1997 | Nash et al. |
| 5,707,393 A | 1/1998 | Kensey et al. |
| 5,722,981 A | 3/1998 | Stevens |
| 5,755,727 A | 5/1998 | Kontos |
| 5,782,861 A | 7/1998 | Cragg et al. |
| 5,797,939 A | 8/1998 | Yoon |
| 5,814,065 A | 9/1998 | Diaz |
| 5,817,074 A | 10/1998 | Racz |
| 5,827,281 A | 10/1998 | Levin |
| 5,860,990 A | 1/1999 | Nobles et al. |
| 5,861,003 A | 1/1999 | Latson et al. |
| 5,868,762 A | 2/1999 | Cragg et al. |
| 5,916,236 A | 6/1999 | Muijs Van de Moer et al. |
| 5,935,147 A | 8/1999 | Kensey et al. |
| 5,941,899 A | 8/1999 | Granger et al. |
| 5,954,732 A | 9/1999 | Hart et al. |
| 5,997,515 A | 12/1999 | de la Torre et al. |
| 6,007,563 A | 12/1999 | Nash et al. |
| 6,033,427 A | 3/2000 | Lee |
| 6,056,768 A | 5/2000 | Cates et al. |
| 6,080,183 A | 6/2000 | Tsugita et al. |
| 6,126,675 A | 10/2000 | Shchervinsky et al. |
| 6,136,010 A | 10/2000 | Modesitt et al. |
| 6,179,863 B1 | 1/2001 | Kensey et al. |
| 6,190,400 B1 | 2/2001 | Van De Moer et al. |
| 6,200,328 B1 | 3/2001 | Cragg et al. |
| 6,206,895 B1 | 3/2001 | Levinson |
| 6,241,768 B1 | 6/2001 | Agarwal et al. |
| 6,245,080 B1 | 6/2001 | Levinson |
| 6,296,658 B1 | 10/2001 | Gershony et al. |
| 6,319,263 B1 | 11/2001 | Levinson |
| 6,350,274 B1 | 2/2002 | Li |
| 6,375,671 B1 | 4/2002 | Kobayashi et al. |
| 6,383,208 B1 | 5/2002 | Sancoff et al. |
| 6,395,015 B1 | 5/2002 | Borst et al. |
| 6,398,796 B2 | 6/2002 | Levinson |
| 6,425,911 B1 | 7/2002 | Akerfeldt et al. |
| 6,461,364 B1 | 10/2002 | Ginn et al. |
| 6,485,481 B1 | 11/2002 | Pfeiffer |
| 6,500,184 B1 | 12/2002 | Chan et al. |
| 6,508,828 B1 | 1/2003 | Akerfeldt et al. |
| 6,520,951 B1 | 2/2003 | Carrillo, Jr. et al. |
| 6,596,012 B2 | 7/2003 | Akerfeldt et al. |
| 6,596,014 B2 | 7/2003 | Levinson et al. |
| 6,596,915 B1 | 7/2003 | Satyapal et al. |
| 6,638,286 B1 | 10/2003 | Burbank et al. |
| 6,669,707 B1 | 12/2003 | Swanstrom et al. |
| 6,669,735 B1 | 12/2003 | Pelissier |
| 6,702,835 B2 | 3/2004 | Ginn |
| 6,730,112 B2 | 5/2004 | Levinson |
| 6,764,500 B1 * | 7/2004 | Muijs Van De Moer ................. A61B 17/0057 606/213 |
| 6,770,070 B1 | 8/2004 | Balbierz |
| 6,779,701 B2 | 8/2004 | Bailly et al. |
| 6,786,915 B2 | 9/2004 | Akerfeldt et al. |
| 6,860,895 B1 | 3/2005 | Akerfeldt et al. |
| 6,890,342 B2 | 5/2005 | Zhu et al. |
| 6,932,824 B1 | 8/2005 | Roop et al. |
| 6,939,363 B2 | 9/2005 | Akerfeldt |
| 6,942,674 B2 | 9/2005 | Belef et al. |
| 6,949,107 B2 | 9/2005 | McGuckin, Jr. et al. |
| 6,949,114 B2 | 9/2005 | Milo et al. |
| 6,964,668 B2 | 11/2005 | Modesitt et al. |
| 6,969,397 B2 | 11/2005 | Ginn |
| 6,984,219 B2 | 1/2006 | Ashby et al. |
| 6,989,022 B2 | 1/2006 | Nowakowski |
| 6,997,940 B2 | 2/2006 | Bonutti |
| 7,001,398 B2 | 2/2006 | Carley et al. |
| 7,001,400 B1 | 2/2006 | Modesitt et al. |
| 7,008,440 B2 | 3/2006 | Sing et al. |
| 7,008,441 B2 | 3/2006 | Zucker |
| 7,008,442 B2 | 3/2006 | Brightbill |
| 7,094,248 B2 | 8/2006 | Bachinski et al. |
| 7,169,168 B2 | 1/2007 | Muijs Van De Moer et al. |
| 7,326,221 B2 | 2/2008 | Sakamoto et al. |
| 7,462,188 B2 | 12/2008 | McIntosh |
| 7,534,248 B2 | 5/2009 | Mikkaichi et al. |
| 7,569,063 B2 | 8/2009 | Bailly et al. |
| 7,662,161 B2 | 2/2010 | Briganti et al. |
| 7,678,133 B2 | 3/2010 | Modesitt |
| 7,753,935 B2 | 7/2010 | Brett et al. |
| 7,846,180 B2 | 12/2010 | Cerier |
| 7,918,868 B2 | 4/2011 | Marshall et al. |
| 7,998,169 B2 | 8/2011 | Modesitt |

(56) References Cited

U.S. PATENT DOCUMENTS

| | | |
|---|---|---|
| 8,002,791 B2 | 8/2011 | Modesitt |
| 8,002,792 B2 | 8/2011 | Modesitt |
| 8,002,793 B2 | 8/2011 | Modesitt |
| 8,012,168 B2 | 9/2011 | Modesitt |
| 8,083,767 B2 | 12/2011 | Modesitt |
| 8,137,380 B2 | 3/2012 | Green et al. |
| 8,177,795 B2 | 5/2012 | Niese et al. |
| 8,241,325 B2 | 8/2012 | Modesitt |
| 8,267,942 B2 | 9/2012 | Szabo et al. |
| 8,361,092 B1 | 1/2013 | Asfora |
| 8,597,324 B2 | 12/2013 | Briganti et al. |
| 8,652,166 B2 | 2/2014 | Åkerfeldt |
| 8,821,507 B2 | 9/2014 | Axelson, Jr. et al. |
| 8,906,050 B2 | 12/2014 | Brett et al. |
| 9,060,751 B2 | 6/2015 | Martin et al. |
| 9,850,013 B2 | 12/2017 | Grant et al. |
| 2001/0044631 A1 | 11/2001 | Akin et al. |
| 2002/0019648 A1 | 2/2002 | Akerfeldt et al. |
| 2002/0019649 A1 | 2/2002 | Sikora et al. |
| 2002/0055767 A1 | 5/2002 | Forde et al. |
| 2002/0107506 A1 | 8/2002 | McGuckin et al. |
| 2002/0169377 A1 | 11/2002 | Khairkhahan et al. |
| 2002/0177864 A1 | 11/2002 | Camrud |
| 2002/0198562 A1 | 12/2002 | Akerfeldt et al. |
| 2003/0050665 A1 | 3/2003 | Ginn |
| 2003/0060846 A1 | 3/2003 | Egnelov et al. |
| 2003/0078598 A1 | 4/2003 | Ginn et al. |
| 2003/0093093 A1 | 5/2003 | Modesitt et al. |
| 2003/0120305 A1 | 6/2003 | Jud et al. |
| 2003/0144695 A1 | 7/2003 | McGuckin et al. |
| 2003/0216756 A1 | 11/2003 | Klein et al. |
| 2004/0082906 A1 | 4/2004 | Tallarida et al. |
| 2004/0092964 A1 | 5/2004 | Modesitt et al. |
| 2004/0092969 A1 | 5/2004 | Kumar |
| 2004/0093025 A1 | 5/2004 | Egnelov |
| 2004/0098044 A1 | 5/2004 | Van de Moer et al. |
| 2004/0133238 A1 | 7/2004 | Cerier |
| 2004/0176798 A1 | 9/2004 | Epstein et al. |
| 2004/0243122 A1 | 12/2004 | Auth et al. |
| 2005/0021055 A1 | 1/2005 | Toubia et al. |
| 2005/0033326 A1 | 2/2005 | Briganti et al. |
| 2005/0070957 A1 | 3/2005 | Das |
| 2005/0143817 A1* | 6/2005 | Hunter .................. A61B 17/11 623/11.11 |
| 2005/0149065 A1 | 7/2005 | Modesitt |
| 2005/0209613 A1 | 9/2005 | Roop et al. |
| 2005/0251201 A1 | 11/2005 | Roue et al. |
| 2005/0267520 A1 | 12/2005 | Modesitt |
| 2005/0273135 A1 | 12/2005 | Chanduszko et al. |
| 2005/0288706 A1 | 12/2005 | Widomski et al. |
| 2006/0100665 A1 | 5/2006 | Von Oepen et al. |
| 2006/0106418 A1 | 5/2006 | Seibold et al. |
| 2006/0142784 A1 | 6/2006 | Kontos |
| 2006/0142797 A1 | 6/2006 | Egnelov |
| 2006/0265008 A1 | 11/2006 | Maruyama et al. |
| 2006/0287673 A1 | 12/2006 | Brett et al. |
| 2007/0112385 A1 | 5/2007 | Conlon |
| 2007/0135826 A1 | 6/2007 | Zaver et al. |
| 2007/0179509 A1 | 8/2007 | Nagata et al. |
| 2007/0179527 A1 | 8/2007 | Eskuri et al. |
| 2007/0197858 A1 | 8/2007 | Goldfarb et al. |
| 2007/0255313 A1 | 11/2007 | Modesitt |
| 2007/0282351 A1 | 12/2007 | Harada et al. |
| 2007/0282373 A1 | 12/2007 | Ashby et al. |
| 2008/0109017 A1 | 5/2008 | Herweck et al. |
| 2008/0228204 A1 | 9/2008 | Hamilton et al. |
| 2008/0243148 A1 | 10/2008 | Mikkaichi et al. |
| 2008/0312646 A9 | 12/2008 | Auth et al. |
| 2009/0012521 A1 | 1/2009 | Axelson, Jr. et al. |
| 2009/0018574 A1 | 1/2009 | Martin |
| 2009/0048559 A1 | 2/2009 | Grathwohl |
| 2009/0088723 A1 | 4/2009 | Khosravi et al. |
| 2009/0112257 A1 | 4/2009 | Preinitz et al. |
| 2009/0143815 A1 | 6/2009 | Eidenschink et al. |
| 2009/0143821 A1 | 6/2009 | Stupak |
| 2009/0312786 A1 | 12/2009 | Trask et al. |
| 2010/0022823 A1 | 1/2010 | Goldfarb et al. |
| 2010/0094425 A1 | 4/2010 | Bentley et al. |
| 2010/0125296 A1 | 5/2010 | Modesitt |
| 2010/0152772 A1 | 6/2010 | Brett et al. |
| 2010/0222796 A1 | 9/2010 | Brett et al. |
| 2010/0228184 A1 | 9/2010 | Mavani et al. |
| 2010/0292717 A1 | 11/2010 | Petter-Puchner et al. |
| 2011/0077667 A1 | 3/2011 | Singhatat et al. |
| 2011/0082495 A1 | 4/2011 | Ruiz |
| 2011/0087270 A1 | 4/2011 | Penner et al. |
| 2011/0224728 A1 | 9/2011 | Martin et al. |
| 2011/0270284 A1 | 11/2011 | Beauchamp et al. |
| 2012/0059399 A1* | 3/2012 | Hoke ............... A61B 17/00491 606/153 |
| 2012/0089166 A1 | 4/2012 | Modesitt |
| 2012/0226308 A1 | 9/2012 | Martin et al. |
| 2012/0226309 A1 | 9/2012 | Jonsson |
| 2012/0296275 A1 | 11/2012 | Martin et al. |
| 2012/0302987 A1 | 11/2012 | Jonsson |
| 2013/0116799 A1* | 5/2013 | Derwin ..................... A61F 2/02 623/23.72 |
| 2013/0218125 A1 | 8/2013 | Stopek et al. |
| 2013/0274795 A1 | 10/2013 | Grant et al. |
| 2014/0018846 A1 | 1/2014 | Grant et al. |
| 2014/0018847 A1 | 1/2014 | Grant et al. |
| 2014/0194926 A1 | 7/2014 | Bailly et al. |
| 2014/0277113 A1* | 9/2014 | Stanley ............... A61B 17/0057 606/213 |
| 2014/0345109 A1 | 11/2014 | Grant et al. |
| 2016/0051239 A1 | 2/2016 | Martin et al. |
| 2016/0166241 A1 | 6/2016 | McGoldrick et al. |
| 2017/0281142 A1 | 10/2017 | Martin et al. |

FOREIGN PATENT DOCUMENTS

| | | |
|---|---|---|
| EP | 0894475 A1 | 2/1999 |
| EP | 1 046 375 A1 | 10/2000 |
| EP | 1879505 A2 | 1/2008 |
| EP | 2260770 A2 | 12/2010 |
| EP | 2 292 147 A1 | 3/2011 |
| EP | 2 628 592 A1 | 8/2013 |
| WO | WO-1994/008513 A1 | 4/1994 |
| WO | WO-00/07520 A1 | 2/2000 |
| WO | WO-2000/033744 A1 | 6/2000 |
| WO | WO-2002/102236 A2 | 12/2002 |
| WO | WO-2004/012601 A2 | 2/2004 |
| WO | WO-2004/012603 A2 | 2/2004 |
| WO | WO-2004/012627 A1 | 2/2004 |
| WO | WO-2006/117766 A2 | 11/2006 |
| WO | WO-2007/011353 A2 | 1/2007 |
| WO | WO-2008/042229 A2 | 4/2008 |
| WO | WO-2008/152617 A2 | 12/2008 |
| WO | WO-2009/149455 A1 | 12/2009 |
| WO | WO-2010/027693 A2 | 3/2010 |
| WO | WO-2010/123821 A1 | 10/2010 |
| WO | WO-2011/080588 A2 | 7/2011 |
| WO | WO-2012/090069 A2 | 7/2012 |
| WO | WO-2012/156819 A2 | 11/2012 |
| WO | WO-2013/007534 A1 | 1/2013 |
| WO | WO-2013/128292 A2 | 9/2013 |
| WO | WO-2013/188351 A2 | 12/2013 |
| WO | WO-2014/141209 A1 | 9/2014 |
| WO | WO-2016/096930 A1 | 6/2016 |
| WO | WO-2016/096932 A1 | 6/2016 |

OTHER PUBLICATIONS

U.S. Appl. No. 62/092,240, filed Dec. 15, 2014, Grant et al.
U.S. Appl. No. 62/092,212, filed Dec. 15, 2014, McGoldrick et al.
European Patent Office Partial Supplementary Search Report. Application No. 12784868.7, dated Jan. 12, 2015, 5 pages.
Extended European Search Report, Application No. EP 11852355.4, dated Sep. 28, 2015, 7 pages.
Grant, et al., Hales' 1733 Haemastaticks, Anesthesiology, 112(1) (2010).
Hales, Stephen, Statical Essays, vol. 2 (1773).

(56) References Cited

OTHER PUBLICATIONS

International Preliminary Report on Patentability, PCT/IB2010/003461, dated Jul. 12, 2012, 10 pages.
International Preliminary Report on Patentability, PCT/IE2006/000043, dated Oct. 30, 2007, 10 pages.
International Search Report, PCT/EP2015/079904, 7 pages, dated Mar. 1, 2016.
International Search Report, PCT/IB2010/003461, dated Oct. 11, 2011, 6 pages.
International Search Report, PCT/IB2011/003295, dated Jun. 29, 2012, 4 pages.
International Search Report, PCT/IB2012/001101, dated Jan. 30, 2013, 3 pages.
International Search Report, PCT/IB2013/000839, dated Jan. 14, 2014, 6 pages.
International Search Report, PCT/IB2014/059848, dated Jul. 7, 2014, 5 pages.
Written Opinion, PCT/EP2015/079904, 8 pages, dated Mar. 1, 2016.
Written Opinion, PCT/IB2010/003461, dated Oct. 11, 2011, 9 pages.
Written Opinion, PCT/IB2011/003295, dated Jun. 29, 2012, 5 pages.
Written Opinion, PCT/IB2012/001101, dated Jan. 30, 2013, 5 pages.
Written Opinion, PCT/IB2013/000839, dated Jan. 14, 2014, 11 pages.
Written Opinion, PCT/IB2014/059848, dated Jul. 7, 2014, 8 pages.
Written Opinion, PCT/IE2006/000043, dated Oct. 29, 2007, 9 pages.

\* cited by examiner

IMPLANTABLE SEALABLE MEMBER WITH MESH LAYER

CROSS REFERENCE TO RELATED APPLICATIONS

The present application is a continuation of U.S. patent application Ser. No. 14/970,284, filed Dec. 15, 2015, which claims priority to, U.S. Provisional Patent Application No. 62/092,212, filed Dec. 15, 2014, the entirety of each of which is hereby incorporated by reference.

BACKGROUND

During a surgical or endoscopic operation on a body lumen, e.g., a blood vessel, an aperture is formed (e.g., from an arteriotomy) in the tissue of the lumen. Following the procedure, the aperture has to be closed in order for the lumen to heal. One relatively new type of closure apparatus has a flexible disc that is delivered into the body lumen to seal the aperture. The disc retains the tissue in apposition until the lumen is healed, allowing the wound to heal from the inside of the lumen.

In certain patient groups, the area surrounding the tissue within the body lumen is diseased and/or has accumulation (e.g., plaque or calcified lesions on the tissue wall). Due to the irregular surface topology of such areas, the effectiveness of the seal made by certain closure apparatuses is reduced, as channels are formed between the disc and the tissue surface.

There are benefits in improving the seal formed by a closure apparatus when closing an aperture formed in the tissue of the body lumen.

SUMMARY

The provided technologies provide an implant closure device having a mesh layer formed on a flexible substrate, collectively forming a sealable member, that improves a seal of an aperture in the body lumen. During closure of the aperture, the sealable member is held against the inner-luminal tissue of the vessel wall such that the textured surface of the mesh layer is oriented against the tissue. The meshing facilitates a faster and more secure adherence of the sealable member to the surrounding edges at the puncture site. Furthermore, the provided technologies promote platelet-capture and encourage platelet aggregation on the mesh layer. The platelet impregnated mesh layer facilitates cellular adhesion, enabling the sealable member to act, in essence, as a "biological glue." Thus, faster time to hemostasis, improved security of the sealing, and improved apposition of the implant to the vessel wall can be obtained.

As demonstrated herein, the provided technologies suggest that faster healing time of the punctured or incised vessel can be achieved. The platelet impregnated mesh layer is observed to encourage localized platelet activation, e.g., when in contact with collagen from the exposed wound, at the wound surface.

As further demonstrated herein, the provided technologies achieve unprecedented acute sealing time in closing a blood vessel and unprecedented reduction of the loss of fluid from such vessel. Acute seal refers to a state of the aperture in which fluids within the vessel are completely sealed within the lumen such that no fluids are seeping or moving through the aperture. Acute sealing time begins when an implant closure device has been deployed to the sealing position and ends when the implant closure device achieves an acute seal. Low acute sealing time reduces the surgery time for a given procedure and reduces the amount of blood loss.

A remarkable feature of the provided technologies is that they enable new types of interventional, surgical, and endoscopic procedures in providing a reliable and consistent closure of an aperture in a body lumen without regard to the tissue surface topography. The nature of the flexible sealable member means it has a significant capability, beyond the state of the art, to provide sealing across a wide variety of blood vessel inner lumen surface topography. This topography can be in various states of disrepair due to disease and systemic diseases (e.g., diabetes). In addition, closure of larger apertures in healthy tissue can also be performed. In certain embodiments, the disclosed technologies are used for closing access site holes in hollow vessels up to 30 French (F), whereby the mesh layer, in a non blood carrying vessel may act as a scaffold for tissue in-growth.

In one aspect, the present disclosure describes an implantable device for sealing an aperture in a tissue of a body lumen (e.g., to close a surgical or endoscopic perforation in a body cavity, such as the gastrointestinal tract, heart, peritoneal cavity, esophagus, vagina, rectum, trachea, bronchi, and blood vessel, e.g., the femoral artery, subclavian artery, ascending and descending aorta, auxiliary and brachial arteries, femoral vein, iliac vein, subclavian vein, and vena cava). The implantable device comprises a sealable member (e.g., flexible wing). The sealable member comprises a flexible substrate and a mesh layer (e.g., of an electrospun material) on the flexible substrate.

The sealable member is positionable against an internal surface of the tissue adjacent the aperture in the tissue when the device is in a sealing position. In certain embodiments, the sealable member is deployed at the aperture such that hemodynamic pressure of the blood within vessel maintains the sealable member in position. In some embodiments, the sealable member is deployed at the aperture such that the hemodynamic or hydraulic pressure of the fluid within the respective vessel or body lumen maintains the sealable member in position.

In some embodiments, the mesh layer comprises an electrospun material. In some embodiments, the mesh layer is structured to promote platelet capture (e.g., whereby the captured platelets encourages localized platelet activation, e.g., when in contact with collagen from the exposed wound, at the wound surface).

In some embodiments, the flexible substrate comprises at least one material selected from the group consisting of an extruded material, a molded material (e.g., via injection or compression molding), and a casted material.

In some embodiments, the sealable member comprises a bioabsorbable polymer film.

In some embodiments, the mesh layer has a first thickness, and the flexible substrate has a second thickness, wherein the second thickness is greater than the first thickness. In certain embodiments, the first thickness (of the mesh layer) is between about 5 µm and about 500 µm, or between about 5 µm and about 750 µm, or between about 5 µm and about 1000 µm, or between about 5 µm and about 1500 µm, or between about 5 µm and about 2000 µm, or between about 5 µm and about 2500 µm, or between about 5 µm and about 3000 µm, or between about 5 µm and about 4000 µm, e.g., depending on the size of the vessel to which the device is placed (e.g., vessels having internal diameters between 5 mm and 30 mm) and/or the size of the aperture to be closed (e.g., between 6 (F) French and 27 (F) French). In such embodiments, the second thickness (of the flexible substrate) is between about 40 µm and about 500 µm, or between about 40 µm and about 750 µm, or between about 40 µm and about 1000 µm, or between about 40 µm and about 1500 µm, or between about 40 µm and about 2,000 µm, or between about 40 µm and about 2500 µm, or between about 40 µm and about 3000 µm, or between about 40 µm and about 4000 µm, respectively e.g., depending also on the size of the vessel and/or the size of the aperture.

In certain embodiments, the first thickness (of the mesh layer) is between about 5 µm and about 3000 µm, or between about 5 µm and 8000 µm, or between about 5 µm and 20,000 µm (and greater), e.g., depending on the size of a non-vascular body lumen (e.g., having an internal diameter between 15 mm and 100+ mm) to which the device is being placed. In such embodiments, the second thickness (of the flexible substrate) is between about 40 µm and about 3000 µm, or between about 40 µm and about 8000 µm, or between about 40 µm and 20,000 µm (and greater), respectively, e.g., depending also on the size of the non-vascular body lumen.

In some embodiments, the mesh layer and the flexible substrate are made of the same material.

In some embodiments, the mesh layer and the flexible substrate are made of different material.

In some embodiments, the mesh layer comprises at least one material selected from the group consisting of Polydioxanone, Poly-L-lactide, Poly-D-lactide, Poly-DL-lactide, Polyglycolide, ε-Caprolactone, Polyethylene glycol, and a copolymer thereof. In some embodiments, the material of the mesh layer is a co-polymer of, for example, but not limited to, Polydioxanone, Poly-L-lactide, Poly-D-lactide, Poly-DL-lactide, Polyglycolide, ε-Caprolactone, and Polyethylene glycol. In certain embodiments, the co-polymer includes (a) monomers of Polydioxanone, Poly-L-lactide, Poly-D-lactide, Poly-DL-lactide, Polyglycolide, ε-Caprolactone, or Polyethylene glycol, and (b) one or more additional monomers. In some embodiments, the (a) and (b) monomers form a polymer that is bioabsorbable.

In some embodiments, the flexible substrate comprises at least one material selected from the group consisting of Polydioxanone, Poly-L-lactide, Poly-D-lactide, Poly-DL-lactide, Polyglycolide, ε-Caprolactone, Polyethylene glycol, and a copolymer thereof. In certain embodiments, the material of the flexible substrate is a co-polymer of, for example, but not limited to, Polydioxanone, Poly-L-lactide, Poly-D-lactide, Poly-DL-lactide, Polyglycolide, ε-Caprolactone, and Polyethylene glycol. In some embodiments, the co-polymer includes (a) monomers of Polydioxanone, Poly-L-lactide, Poly-D-lactide, Poly-DL-lactide, Polyglycolide, ε-Caprolactone, or Polyethylene glycol, and (b) one or more additional monomers. In some embodiments, the (a) and (b) monomers form a polymer that is bioabsorbable.

In some embodiments, the sealable member is disposed against the internal surface of the tissue adjacent the aperture such that the mesh layer is in contact with the internal surface, when the closure device is deployed at the sealing position.

In some embodiments, the sealable member is disposed against the internal surface of the tissue adjacent the aperture such that the flexible substrate is in contact with the internal surface, when the closure device is deployed at the sealing position.

In certain embodiments, implantable device further comprises an anchorable member. In some embodiments, the sealable member is deployed at the aperture such that hemodynamic pressure maintains the sealable member in position while the anchorable member is positionable against the sealable member to retain the device at the sealing position, e.g., to prevent the formation of embolism due to a dislodgement or movement of the device in the vessel/lumen, e.g., due to an inadvertent impact near the aperture and/or movements of the patient, following the deployment of the sealable member. In some embodiments, the anchorable member comprises a rigid or flexible support member that contacts the sealable member when the sealable member.

In some embodiments, the sealable member is disposed against the anchorable member such that the mesh layer engages against the internal surface of the tissue adjacent the aperture when the device is in the sealing position.

In some embodiments, the sealable member is disposed against the anchorable member such that the flexible substrate engages against the internal surface of the tissue adjacent the aperture when the device is in the sealing position.

In some embodiments, the mesh layer comprises a plurality of fibers having a diameter in the range from 0.3 µm to 8 µm. In certain embodiments, the plurality of fibers makes up less than 50% of the volume of the mesh layer. In certain embodiments, the plurality of fibers makes up from 5 volume % to 25 volume %, or from 1 volume % to 35 volume % of the mesh layer.

In some embodiments, a substantial portion (e.g., greater than 50%) of the fibers has a random orientation.

In some embodiments, a substantial portion (e.g., greater than 50%) of the fibers has a patterned orientation.

In some embodiments, the mesh layer comprises a plurality of fibers structured (e.g., sized and shaped) to promote platelet capture (e.g., whereby the captured platelets encourages localized platelet activation, e.g., due to the contact with collagen from the exposed wound, at the wound surface) when the device is in the sealing position. In some embodiments, the material of the mesh layer has low thrombogenicity, whereby the mesh layer forms a non-thrombogenic surface. Thrombogenicity, as used herein, refers to a tendency or propensity to produce coagulation of the blood, especially as predisposing to thrombosis. In certain embodiments, the plurality of fibers makes up from 5 volume % to 25 volume %, or from 1 volume % to 35 volume % of the mesh layer.

In some embodiments, the sealable member comprises a textured surface (e.g., on the mesh layer or the flexible substrate) to engage against the internal surface of the tissue adjacent the aperture.

In some embodiments, the sealable member is sized to seal an arteriotomy of an arterial lumen.

In some embodiments, the sealable member is structured (e.g., sized and shaped) to flexibly roll when in a delivery configuration such that a delivery cross-sectional area of the rolled sealable member has a diameter smaller than that of the aperture.

In another aspect, the present disclosure describes a method for sealing an aperture in a tissue of a body lumen (e.g., to close a surgical or endoscopic perforation in a body cavity, such as the gastrointestinal tract, heart, peritoneal cavity, esophagus, vagina, rectum, trachea, bronchi, and blood vessel, e.g., the femoral artery, subclavian artery, ascending and descending aorta, auxiliary and brachial arteries, femoral vein, iliac vein, subclavian vein, and vena cava).

The method comprises deploying a sealable member of an implantable closure device (e.g., causing a flexible wing to unfold) from a delivery state to a sealable state within the body lumen, wherein the delivery state of the sealable member has a first flex profile so as to fit through the aperture, and wherein the sealable state of the sealable member has a second curved profile so as to form a tamponade of the aperture when the sealable member is engaged against an interior luminal surface of the tissue adjacent the aperture when the device is in a sealing position. The method then includes positioning the sealable member against the interior luminal surface of the tissue adjacent the aperture to form the tamponade at the sealing position over the aperture, wherein the sealable member comprises a flexible substrate and a mesh layer (e.g., of an electrospun material) formed on the flexible substrate (e.g., such that the mesh layer remains, e.g., bonded, connected, and/or attached to the flexible substrate to bend as a single structure with the flexible substrate), wherein the mesh layer comprises a plurality of fibers structured (e.g., sized and shaped) to promote platelet capture (e.g., whereby the captured platelets encourages localized platelet activation, e.g., with collagen from the exposed wound, at the wound surface). In certain embodiments, the plurality of fibers makes up from 5 volume % to 25 volume %, or from 1 volume % to 35 volume % of the mesh layer.

In some embodiments, the mesh layer comprises a plurality of randomly-oriented fibers having diameters in the range of about 0.3 μm to 8 μm.

In some embodiments, the mesh layer comprises a plurality of patterned fibers having diameters in the range of about 0.3 μm to 8 μm.

In some embodiments, the sealable member is deployed at the aperture such that hemodynamic pressure maintains the sealable member in position.

In some embodiments, the method includes maintaining the position of the sealable member at the interior luminal surface of the tissue adjacent the aperture at the sealing position (e.g., to prevent dislodgment of the sealable member from the sealing position due to inadvertent external impact near the aperture and/or movement of the patient) (e.g., by positioning an anchorable member against the sealable member and maintaining the support member positionably fixed at the sealing position).

In some embodiments, the anchorable member exerts no force on the sealable member when the sealable member is in the sealing position. Alternatively, in certain embodiments, the anchorable member comprises a support surface to hold the sealable member against the interior surface of the tissue when the device is in the sealing position (e.g., wherein the anchorable member comprises a guard member, e.g., an insertable or engageable pin or cage).

In some embodiments, the mesh layer has a first thickness (e.g., between about 10 and 60 μm), and the flexible substrate has a second thickness (e.g., between about 60 and 120 μm), wherein the second thickness is greater than the first thickness. In certain embodiments, the first thickness (of the mesh layer) is between about 5 μm and about 500 μm, or between about 5 μm and about 750 μm, or between about 5 μm and about 1000 μm, or between about 5 μm and about 1500 μm, or between about 5 μm and about 2000 μm, or between about 5 μm and about 2500 μm, or between about 5 μm and about 3000 μm, or between about 5 μm and about 4000 μm, e.g., depending on the size of the vessel to which the device is placed (e.g., vessels having internal diameters between 5 mm and 30 mm) and/or the size of the aperture to be closed (e.g., between 6 (F) French and 27 (F) French). In such embodiments, the second thickness (of the flexible substrate) is between about 40 μm and about 500 μm, or between about 40 μm and about 750 μm, or between about 40 μm and about 1000 μm, or between about 40 μm and about 1500 μm, or between about 40 μm and about 2,000 μm, or between about 40 μm and about 2500 μm, or between about 40 μm and about 3000 μm, or between about 40 μm and about 4000 μm, respectively e.g., depending also on the size of the vessel and/or the size of the aperture.

In some embodiments, the flexible substrate comprises at least one material selected from the group consisting of an extruded material, an injection molded, a compression molded, and a casted material.

In some embodiments, the mesh layer comprises an electrospun material, and the flexible substrate comprises a material selected from the group consisting of an extruded material, a molded material (e.g., via compression molding, injection molding, etc.), and a casted material.

In some embodiments, the mesh layer comprises at least one material selected from the group consisting of Polydioxanone, Poly-L-lactide, Poly-D-lactide, Poly-DL-lactide, Polyglycolide, ε-Caprolactone, Polyethylene glycol, and a copolymer thereof. In some embodiments, the material of the mesh layer is a co-polymer of, for example, but not limited to, Polydioxanone, Poly-L-lactide, Poly-D-lactide, Poly-DL-lactide, Polyglycolide, ε-Caprolactone, and Polyethylene glycol. In some embodiments, the co-polymer includes (a) monomers of Polydioxanone, Poly-L-lactide, Poly-D-lactide, Poly-DL-lactide, Polyglycolide, ε-Caprolactone, or Polyethylene glycol, and (b) one or more additional monomers. In some embodiments, the (a) and (b) monomers form a polymer that is bioabsorbable.

In some embodiments, the flexible substrate comprises at least one material selected from the group consisting of Polydioxanone, Poly-L-lactide, Poly-D-lactide, Poly-DL-lactide, Polyglycolide, ε-Caprolactone, Polyethylene glycol, and a copolymer thereof. In some embodiments, the material of the flexible substrate is a co-polymer of, for example, but not limited to, Polydioxanone, Poly-L-lactide, Poly-D-lactide, Poly-DL-lactide, Polyglycolide, ε-Caprolactone, and Polyethylene glycol. In some embodiments, the co-polymer includes (a) monomers of Polydioxanone, Poly-L-lactide, Poly-D-lactide, Poly-DL-lactide, Polyglycolide, ε-Caprolactone, or Polyethylene glycol, and (b) one or more additional monomers. In some embodiments, the (a) and (b) monomers form a polymer that is bioabsorbable.

In another aspect, the present disclosure describes a method of manufacturing a sealable member of an implant. The method comprises forming (e.g., by an extrusion process; a molding process, e.g., compression molding, injection molding; or a casting process) a flexible substrate. In some embodiments, the flexible substrate is configured to (i) flexibly bend such that opposing ends of the flexible substrate can overlap when under load and to (ii) return to an original shape of the flexible substrate when the load is removed. The method then includes forming (e.g., by an electrospun process) a mesh layer on the flexible substrate. In some embodiments, a portion of the fibers of the mesh layer is porous.

In certain embodiments, the mesh layer is formed with a first thickness (e.g., between about 10 and 60 μm) and the flexible substrate is formed with a second thickness (e.g., between about 60 and 120 μm), wherein the first thickness is smaller than the second thickness.

In some embodiments, the mesh layer has a thickness between about 5 μm and about 500 μm, or between about 5 μm and about 750 μm, or between about 5 μm and about 1000 μm, or between about 5 μm and about 1500 μm, or between about 5 μm and about 2000 μm, or between about 5 μm and about 2500 μm, or between about 5 μm and about 3000 μm, or between about 5 μm and about 4000 μm. In such embodiments, the second thickness (of the flexible substrate) is between about 40 μm and about 500 μm, or between about 40 μm and about 750 μm, or between about 40 µm and about 1000 µm, or between about 40 µm and about 1500 µm, or between about 40 µm and about 2,000 µm, or between about 40 µm and about 2500 µm, or between about 40 µm and about 3000 µm, or between about 40 µm and about 4000 µm, respectively.

In some embodiments, the mesh layer comprises a plurality of fibers structured (e.g., sized and shaped) to promote platelet capture (e.g., whereby the captured platelets encourages localized platelet activation, e.g., when in contact with collagen from the exposed wound, at the wound surfaces) when the device is in the sealing position. In certain embodiments, the plurality of fibers makes up from 5 volume % to 25 volume %, or from 1 volume % to 35 volume % of the mesh layer.

In some embodiments, the mesh layer comprises a plurality of randomly-oriented fibers having diameters in the range of about 0.3 µm to 8 µm.

In some embodiments, the mesh layer comprises a plurality of patterned fibers having diameters in the range of about 0.3 µm to 8 µm.

In certain embodiments, the mesh layer comprises an electrospun material. In some embodiments, the electrospun material comprises one or more fibers.

In certain embodiments, the flexible substrate comprises an extrude material, a molded material (e.g., via compression molding, injection molding, etc.), and/or a casted material.

In some embodiments, the mesh layer comprises an electrospun material, and the flexible substrate comprises a material selected from the group consisting of an extruded material, a molded material, and a casted material.

In some embodiments, the mesh layer or the flexible substrate comprises at least one material selected from the group consisting of Polydioxanone, Poly-L-lactide, Poly-D-lactide, Poly-DL-lactide, Polyglycolide, ε-Caprolactone, and Polyethylene glycol. In some embodiments, the material of the mesh layer or flexible substrate is a co-polymer of, for example, but not limited to, Polydioxanone, Poly-L-lactide, Poly-D-lactide, Poly-DL-lactide, Polyglycolide, ε-Caprolactone, and Polyethylene glycol. In some embodiments, the co-polymer includes (a) monomers of Polydioxanone, Poly-L-lactide, Poly-D-lactide, Poly-DL-lactide, Polyglycolide, ε-Caprolactone, or Polyethylene glycol, and (b) one or more additional monomers. In some embodiments, the (a) and (b) monomers form a polymer that is bioabsorbable.

In some embodiments, the sealable member is sized such that the sealable member forms a tamponade of the aperture when the sealable member is positioned against an interior luminal surface of the tissue adjacent the aperture.

Further features and aspects of example embodiments of the present invention are described in more detail below.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable and/or bioabsorbable.

As used herein, "bioabsorbable" materials are those that, when introduced into cells, are broken down by cellular machinery (e.g., enzymatic degradation) or by hydrolysis into components that cells can either reuse, reabsorb, or dispose of without significant toxic effects on the cells. In certain embodiments, components generated by breakdown of a bioabsorbable material do not induce inflammation and/or other adverse effects in vivo. In some embodiments, bioabsorbable materials are enzymatically broken down. Alternatively or additionally, in some embodiments, bioabsorbable materials are broken down by hydrolysis. In some embodiments, bioabsorbable polymeric materials break down into their component polymers and/or monomers. In some embodiments, breakdown of bioabsorbable materials (including, for example, bioabsorbable polymeric materials) includes hydrolysis of ester bonds. In some embodiments, breakdown of materials (including, for example, bioabsorbable polymeric materials) includes cleavage of urethane linkages.

As used herein, "implant" is an object that is placed within a subject during a medical operation. The object may be biodegradable and/or bioabsorbable.

As used herein, "mesh" materials are those that, when introduced into a blood vessel, promote platelet capture (e.g., whereby the captured platelets encourages localized platelet activation, e.g., due to the contact with the collagen from the exposed wound, at the wound surface).

The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

The term "sample" refers to a volume or mass obtained, provided, and/or subjected to analysis. In some embodiments, a sample is or comprises a tissue sample, cell sample, a fluid sample, and the like. In some embodiments, a sample is taken from a subject (e.g., a human or animal subject). Those of ordinary skill in the art will appreciate that, in some embodiments, a "sample" is a "primary sample" in that it is obtained from a source (e.g., a subject); in some embodiments, a "sample" is the result of processing of a primary sample, for example to remove certain potentially contaminating components and/or to isolate or purify certain components of interest.

As used herein, the term "substantially", and grammatic equivalents, refer to the qualitative condition of exhibiting at least a majority and total or near-total extent or degree of a characteristic or property of interest. One of ordinary skill in the art will understand that material and chemical phenomena rarely, if ever, go to completion and/or proceed to completeness or achieve or avoid an absolute result.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

Figures are presented herein for illustration purposes only, not for limitation.

BRIEF DESCRIPTION OF THE DRAWING

The Drawing, which is comprised of at least the following Figures, is for illustration purposes only, not for limitation.

DETAILED DESCRIPTION

As described herein, illustrative embodiments provide a vascular closure implantable device for sealing an aperture in a tissue of a body lumen. Examples of the blood vessel includes, but not limited to, the femoral artery, subclavian artery, ascending and descending aorta, auxiliary and brachial arteries, femoral vein, iliac vein, subclavian vein, and vena cava. In some embodiments, the systems, devices, and methods are used to close a surgical perforation in a body cavity, such as the gastrointestinal tract, heart, peritoneal cavity, esophagus, vagina, rectum, trachea, bronchi, and blood vessel.

Figure 1A:
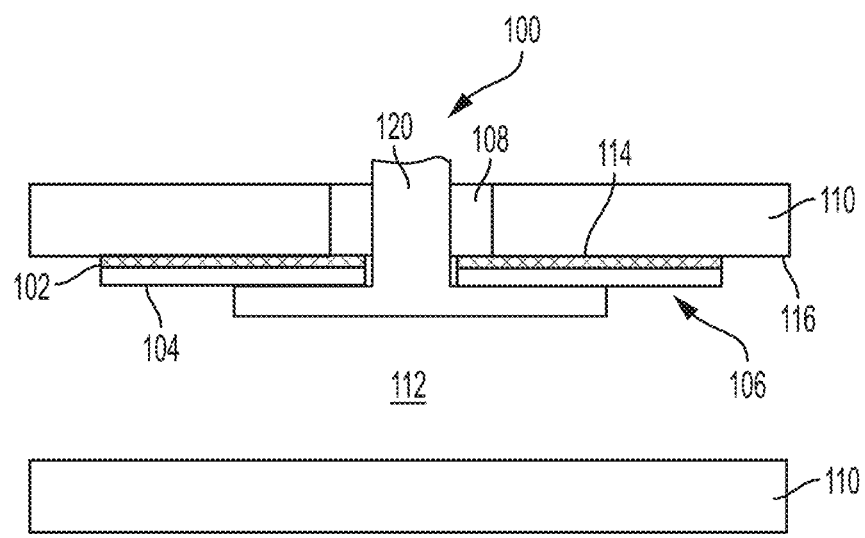
FIG. 1A is a diagram of an exemplary closure device with a material system comprising a mesh layer and a substrate that, collectively, form a sealable member for closing an aperture in a body lumen, according to an illustrative embodiment.

FIG. 1A is a diagram of an exemplary closure device 100 with a material system comprising a mesh layer 102 and a substrate 104 that, collectively, form a sealable member 106 for closing an aperture 108 in a tissue 110 of a body lumen 112.

Examples of the flexible sealable member (also referred to as a "flexible wing") are described in U.S. Patent Application Publication No. 2014/0018847, titled "Percutaneous Perforation Closure Systems, Devices, and Methods," the content of which is incorporated by reference herein in its entirety. Among other things, this disclosure provides details of a variant of the flexible wing design.

The sealable member 106 with the mesh layer 102 and substrate 104 forms, in some embodiments, a flexible bilayer bioabsorbable polymer film. The sealable member 106 is deployable at a sealing position in the body lumen 112. In some embodiments, the mesh layer 102 is formed of a bioabsorbable or biodegradable polymer that is electrospun onto a substrate material 104. The electrospinning process creates and/or forms a textured surface 114, by the mesh layer 102, for contacting the interior surface 116 of the 110 tissue.

Electrospinning employs, in some embodiments, electrical force to draw very fine fibers (e.g., micro or nano-scale) of polymers, ceramics, metals, carbon and/or composite materials from a liquid and/or a solution/melt. Electrospinning typically generates a jet in a high-voltage field to produce elongated fibers. A high-voltage electrical field is applied between a capillary where a suitable solution or melt is stored and a collection screen on which an electrically charged jet solidifies. For example, one electrode from a high-voltage source may be contacted with the solution/melt (e.g., needle, capillary) and the other attached to the collection screen. When a voltage is applied to a droplet of the solution/melt, the droplet is stretched into a jet due to electrostatic repulsion and surface tension. The jet is whipped by electrostatic repulsion until it is deposited on the collection screen. Electrospinning can be adjusted to produce continuous liquid jets by controlling parameters (e.g., molecular weight, viscosity, conductivity, surface tension, and electric potential, flow rate, concentration, distance between capillary and collection screen, temperature, needle gauge, etc.). The method beneficially ensures, among other benefits as described herein (e.g., combined with secondary processing (e.g., reduced pressure processing), that no solvent made from the manufacturing process is carried over into the final product. Of course, other methods of generating very fine fibers may be employed. The mesh layer 102 and/or the substrate 104 comprise, in some embodiments, at least one material selected from the group consisting of Polydioxanone, Poly-L-lactide, Poly-D-lactide, Poly-DL-lactide, Polyglycolide, ε-Caprolactone, Polyethylene glycol, and a copolymer thereof. In some embodiments, the material of the mesh layer 102 and/or substrate layer 104 is a copolymer of, for example, but not limited to, Polydioxanone, Poly-L-lactide, Poly-D-lactide, Poly-DL-lactide, Polyglycolide, ε-Caprolactone, and Polyethylene glycol. In some embodiments, the copolymer includes (a) monomers of Polydioxanone, Poly-L-lactide, Poly-D-lactide, Poly-DL-lactide, Polyglycolide, ε-Caprolactone, or Polyethylene glycol, and (b) one or more additional monomers. In some embodiments, the (a) and (b) monomers form a polymer that is bioabsorbable. One of ordinary skill in the art will appreciate that other bioabsorbable and/or biodegradable material may be employed.

A bioabsorbable polymer can have crystalline and amorphous regions and are therefore, in general, semi-crystalline in nature. Degradation of a bioabsorbable polymer, in certain embodiments, initiates in the amorphous regions, with the crystalline regions degrading at a slower rate relative to the amorphous regions. Without wishing to be tied to a particular theory, and for illustrative purposes only, degradation of a polymer such as Polydioxanone (PDO) occurs along the polymer back bone by hydrolysis of the ester bonds. This non-specific ester bond scission may occur randomly along the polymer chain with water penetration initially breaking the chemical bonds and converting the long polymer chains into natural monomeric acids found in the body, such as lactic acid. Such monomeric acids are then phagocytized by the enzymatic action of special types of mononuclear and multinuclear white blood cells. The polymer is, thus, degraded into non-toxic, low molecular weight residues that are capable of being eliminated from the body by normal metabolic pathways, e.g., via exhalation and/or excretion. Such a pathway thereby enables reference to the breakdown of such polymers in-vivo through terminology such as absorbable, bioabsorbable, degradation, biodegradation, resorbtion, bioresorbtion, among others.

In certain embodiments, the extruded layer 104 preferably has a range between about 60 μm and about 120 μm in thickness. The range of thicknesses may be between 5 μm and 4000 μm. In certain embodiments, the electrospun layer 102 substantially consists of fibers in the range from 0.3 μm to 8 μm diameter, with a layer thickness preferably in the range from 10 μm to 60 μm. The fibers may be arranged in a random or patterned orientation. The range of thicknesses of the mesh layer 102 may be between 5 μm and 4000 μm, e.g., depending on the size of aperture being sealed and/or the size of blood vessel/hollow vessel.

The thickness of the mesh layer 102 and the substrate 104 is such that the sealable member 106 can bend, in some embodiments, to conform to the interior surface of the blood vessel while sufficiently rigid to maintain the tamponade at the aperture 108 when the device 100 is in the sealing position. In some embodiments, the mesh layer 102 and substrate 104 can roll, e.g., such that the tips of the sealable member touch each other, or bend beyond the curvature required to conform to the interior surface of the blood vessel, allowing the sealable member to fit within a delivery cannula to be deployed into the body lumen.

Figure 1B:
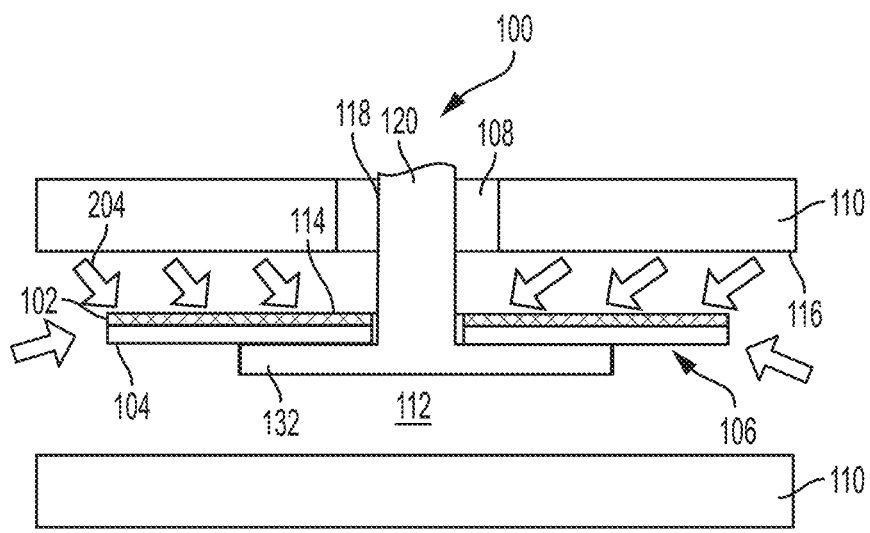
FIG. 1B is a diagram of an exemplary closure device of FIG. 1A during deployment into a body lumen.

FIG. 1B is a diagram of the closure device 100 with a material system comprising the mesh layer 102 and the substrate 104, when introduced into a vessel 112. Without wishing to be bounded to a particular theory, from the mesh structure, the electrospun side 114 of the flexible wing 106 has a larger (textured) surface area compared to an untreated smooth surface of the substrate 104, on the other side of the wing 106. This large surface area promotes platelet capture due to the pore size in the textured surface (e.g., whereby the captured platelet encourages localized platelet activation, e.g., due to contact with the collagen from the exposed wound, at the wound surface). During closing of the hole in the blood vessel 110, the wing 106 is appositioned against the tissue 110 at the hole 108 such that the textured flexible wing surface 114 is positioned against the inner lumen 116 of the vessel tissue 110. The textured surface 114 facilitates a faster and more secure adherence of the flexible wing 106 to the surrounding edges at the puncture site. The electrospun surface 114 of the wing 106 promotes a faster hemostatic seal between the wing 106 and the vessel inner luminal surface 116. The nature of the flexible wing 106 means it has a significant capability, beyond the state of the art, to provide sealing across a wide variety of blood vessel inner lumen surface topography. This topography can be in various states of disrepair due to disease and systemic diseases (e.g., diabetes). The electrospun surface 114 facilitates cellular adhesion, thereby acting as a "biological glue" and would aid encapsulation of the implant 100 in the vessel 110.

Figure 13:
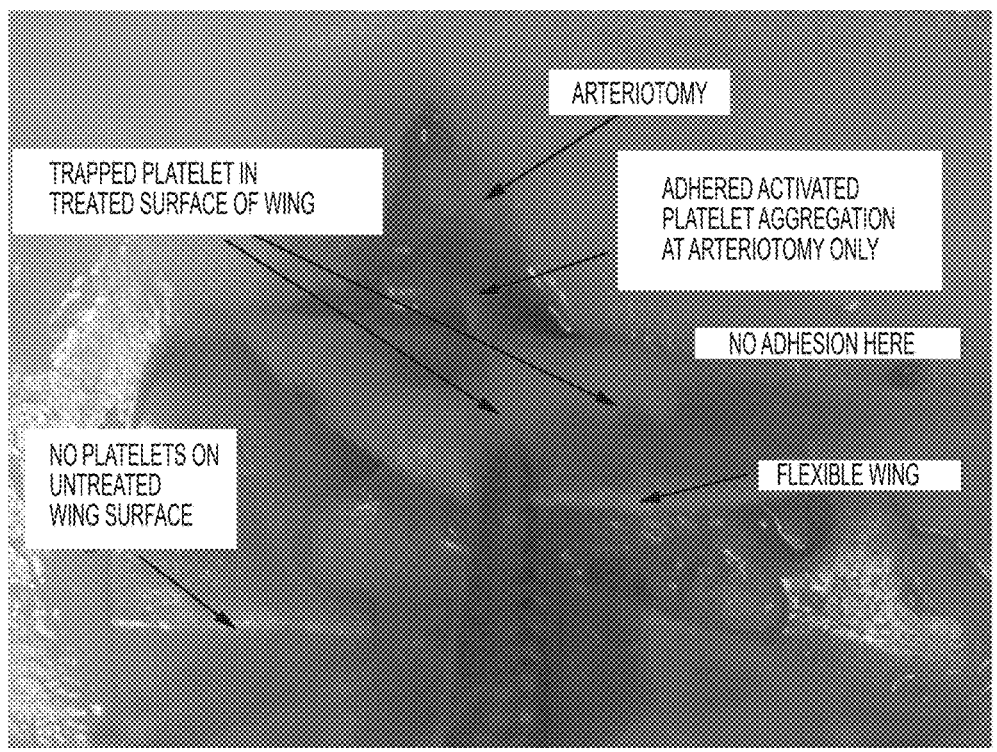
FIG. 13 shows an image of a flexible wing with the mesh layer having been deployed at the site of a 24 (F) French arteriotomy in a pig aorta. The image was captured, after the aorta was explanted, approximately 24 hours after the flexible wing has been deployed at the arteriotomy. The image shows the wing being pulled back at the arteriotomy site. Remarkably, as shown, activated platelets have adhered to the collagen surface of the arteriotomy, creating fibrins at the site. The flexible wing with the mesh layer thus, has facilitated formation of a biological glue which adheres the flexible wing to the arteriotomy site.

FIG. 13 shows an image of a flexible wing 106 with the mesh layer 102 having been deployed at the site of a 24 (F) French arteriotomy in a pig aorta. The image was captured, after the aorta was explanted, approximately 24 hours after the flexible wing 106 has been deployed at the arteriotomy. The image shows the wing being pulled back at the arteriotomy site. Remarkably, as shown, activated platelets have adhered to the collagen surface of the arteriotomy, creating fibrins at the site. The flexible wing 106 with the mesh layer 102 has, thus, biologically glued the tissue together within a short period of time following the closure procedure.

As further shown in FIG. 13, little or no adhesion of the sealable member 106 is observed, in this image, at the unbroken surfaces surrounding the arteriotomy. The activated platelets aggregated on the mesh layer 102 are observed to adhere to the collagen surface of the arteriotomy only.

It is further observed, in this image, within this post-procedure time period, that little or no platelet aggregates on the non-mesh surface of the substrate of the sealable member.

In certain embodiments, the mesh layer 102 preferably has a thickness in the range of about 10 μm (microns) to about 60 μm, including 10, 15, 20, 25, 30, 35, 40, 45, 50, 55 and 60 um. The mesh layer 102, in some embodiments, comprises electrospun fibers that are substantially (e.g., greater than 50% of the fibers) in the range of about 0.3 μm to about 8 μm in diameter. In some embodiments, the spacing between the fibers may be about or greater than 2-3 um. It should be appreciated that other thicknesses and spacing among the fibers may be employed so as to promote platelet capture and/or aggregation (e.g., thereby encouraging localized platelet activation, e.g., due to the contact with the collagen from the exposed wound, at the wound surface).

In certain embodiments, the thickness of the mesh and substrate layers, as deployed in the lumen/vessel, is selected based on the size of the aperture to be sealed and/or the size of the blood vessel/hollow vessel. Table 1 lists exemplary ranges of thicknesses of the mesh and substrate layer that may be selected for a sealable member to close an aperture based on the aperture/incision size that is formed. Table 2 lists exemplary ranges of thicknesses of the mesh and substrate layer that may be selected for a sealable member to close an aperture based on the vessel diameter size. Table 3 lists exemplary ranges of thicknesses of the mesh and substrate layer that may be selected for a sealable member to close an aperture base on the size of the hollow vessel.

TABLE 1

Example thicknesses of the mesh and substrate layers of a sealable member for closure of a blood vessel (e.g., having an internal diameter between about 6 and 12 mm), selected based on the incision/puncture size at the blood vessel.

| French size | Hole Size (mm) | Mesh Layer Thickness (mm) | | Substrate Layer Thickness (mm) | |
|---|---|---|---|---|---|
| | | Min | Max | Min | Max |
| 6 | 2 | 0.005 | 0.5 | 0.04 | 0.5 |
| 9 | 3 | 0.005 | 0.75 | 0.04 | 0.75 |
| 12 | 4 | 0.005 | 1 | 0.04 | 1 |
| 15 | 5 | 0.005 | 1.5 | 0.04 | 1.5 |
| 18 | 6 | 0.005 | 2 | 0.04 | 2 |
| 21 | 7 | 0.005 | 2.5 | 0.04 | 2.5 |
| 24 | 8 | 0.005 | 3 | 0.04 | 3 |
| 27 | 9 | 0.005 | 4 | 0.04 | 4 |

TABLE 2

Example thicknesses of the mesh and substrate layers of a sealable member for closure of a blood vessel, selected based on the size of the blood vessel.

| Vessel Size (Internal Diameter, mm) | Mesh Layer Thickness (mm) | | Substrate Layer Thickness (mm) | |
|---|---|---|---|---|
| | Min | Max | Min | Max |
| 5 | 0.005 | 0.5 | 0.04 | 0.5 |
| 6 | 0.005 | 0.75 | 0.04 | 0.75 |
| 7 | 0.005 | 1 | 0.04 | 1 |
| 9 | 0.005 | 1.5 | 0.04 | 1.5 |
| 11 | 0.005 | 2 | 0.04 | 2 |
| 15 | 0.005 | 3 | 0.04 | 3 |
| 20 | 0.005 | 3.5 | 0.04 | 3.5 |
| 30 | 0.005 | 4 | 0.04 | 4 |

TABLE 3

Example thicknesses of the mesh and substrate layers of a sealable member for closure of a non-blood carrying hollow vessel (e.g., having an internal diameter between 15 and 100+ mm), selected based on the size of the hollow vessel.

| Vessel Size (Internal Diameter, mm) | Mesh Layer Thickness (mm) | | Substrate Layer Thickness (mm) | |
|---|---|---|---|---|
| | Min | Max | Min | Max |
| 15 | 0.005 | 3 | 0.04 | 3 |
| 40 | 0.005 | 8 | 0.04 | 8 |
| >100 | 0.005 | 20+ | 0.04 | 20+ |

Referring still to FIG. 1B, in certain embodiments, the sealable member 106 is maintained in the sealing position at the aperture 108 by the hemostatic pressure of the blood of the vessel 112 (or hydraulic pressure of the fluid of the vessel/lumen). The sealable member 106 may operate, in some embodiments, in conjunction with an anchorable member 120 (as part of the closure device 100), which maintains the sealable member 106 at the sealing position and prevents the inadvertent dislodgment and/or movement of the sealable member 106 from such position, e.g., due to a physical impact near the aperture 108 and/or movements of the patient. Put another way, the anchorable member 120 acts, in some embodiments, as a safety device to prevent the closure device 100 from forming an embolism in the vessel/lumen if the closure device (or portion thereof) is inadvertently dislodged from its deployed position.

In certain embodiments, the anchorable member 120 has a column portion 118 that is disposed in the aperture 108 when the device 100 is in the sealing position. The anchorable member 120 includes, in some embodiments, a rigid or flexible portion 132 to retain the sealable member 106 at the position. In some embodiments, the portion 132 does not exert a force on the sealable member 106 when the device is deployed at the sealing position. In other embodiments, the core portion 132 provides a force to push the sealable member 106 against the tissue 110. In certain embodiments, the force is compressive.

In certain embodiments, the column portion 118 (or portions thereof) and/or core portion 132 (or portions thereof) of the anchorable member 120 comprise a mesh layer, as described herein. In other embodiments, the column portion 118 and/or core portion 132 comprises a body having mesh properties of the mesh layer 102, as described herein.

Figure 2:
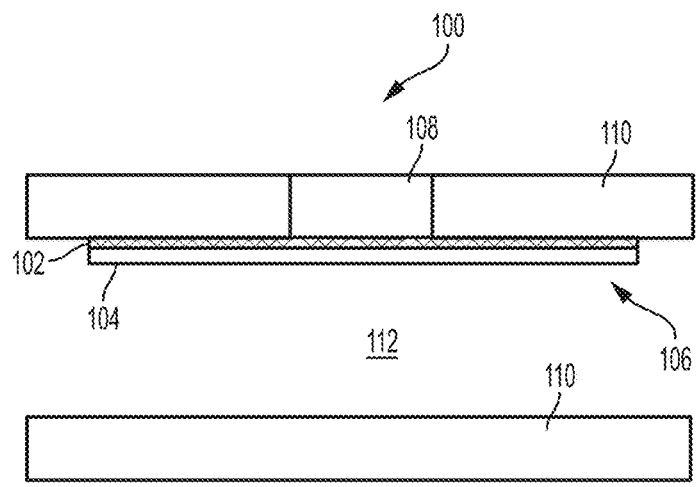
FIG. 2 is a diagram of an exemplary closure device with a material system comprising a mesh layer and a substrate that, collectively, form a sealable member for closing an aperture in a body lumen, according to another illustrative embodiment.

In certain embodiments, the sealable member 106 forms a solid flexible structure. It does not include a hole. FIG. 2 is a diagram of an exemplary closure device 100 with a material system comprising the mesh layer 102 and the substrate 104 that, collectively, form the sealable member 106 for closing an aperture in a body lumen, according to another illustrative embodiment.

In certain embodiments, the closure device 100 is employed for endoscopic procedures.

FIGS. 3A, 3B, 3C, 3D, and 3E are diagrams of material systems comprising a mesh layer 102 and a substrate 104 that, collectively, form a sealable member 106, according to various embodiments. As shown, in FIG. 3A, the mesh layer 102 is formed over a surface 302 of the substrate 104. The sealable member 106 may include a center through-hole 130 for assembly onto the closure device 100. In some embodiments, the material of the mesh layer 102 and the substrate 104 are the same.

Figure 3A:
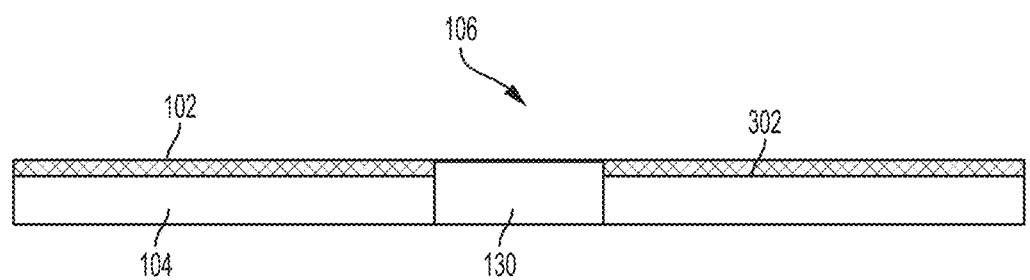
FIGS. 3A, 3B, 3C, 3D, and 3E are diagrams of a material system comprising a mesh layer and a substrate that, collectively, form a sealable member, according to various embodiments.
Figure 3B:
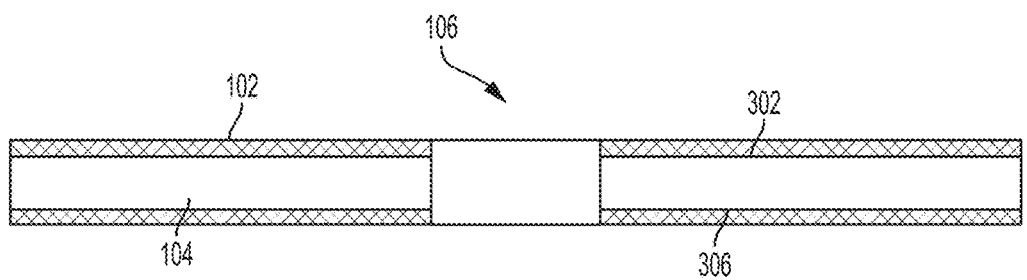

As shown in FIG. 3B, the mesh layer 102 is formed over the surface 302 of the substrate 104. In addition, a second mesh layer 304 is formed over a second surface 306 on the underside of the substrate 104.

Figure 3C:
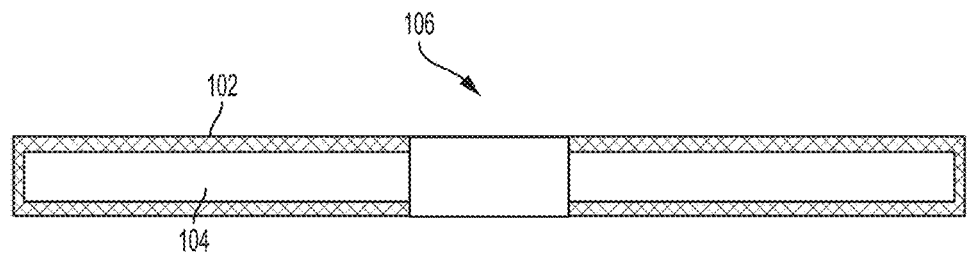

As shown in FIG. 3C, the mesh layer 102 is formed over the substrate 104 so as to encapsulate the substrate 104.

Figure 3D:
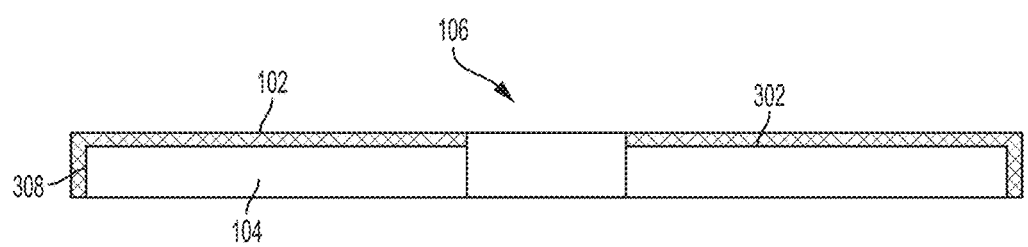

As shown in FIG. 3D, the mesh layer 102 is formed over the substrate 104 so as to encapsulate one side of the substrate 104, including the surface 302 and the side surface 308.

In some embodiments, the sealable members 106 shown in FIGS. 3C and 3D are cut to form the respective sealable members 106 shown in FIGS. 3A and 3B.

Figure 3E:
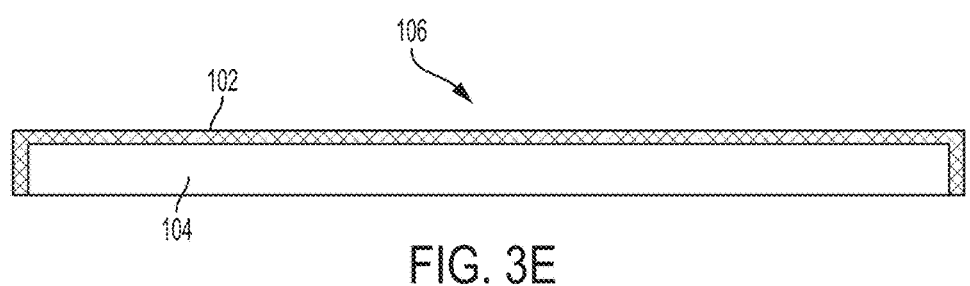

As shown, in FIG. 3E, the mesh layer 102 is formed over a surface 302 of a solid substrate 310 so as to form a single solid structure. In certain embodiments, the single solid structure is employed as the sealable member 106. In some embodiments, the hole 130, e.g., as shown in FIG. 3A, is formed, e.g., by removing and/or cutting the material from the structure, to form the sealable member.

It should be appreciated that in some embodiments, the material of the mesh layer 102 and the substrate 104 are different. In such embodiments, the mesh layer 102, when formed over the substrate 104, has sufficient bond strength to not delaminate when bent during the delivery of the sealable member 106 into the lumen 112 or during the deployment of the sealable member 106 over the aperture of the tissue 110 when the device is in the seal position. In some embodiments, a bioabsorbable and/or biodegradable intermediary material is used between the mesh layer 102 and the substrate 104.

In addition, it should be appreciated that, in certain embodiments, the mesh layer 102 may form within the hole 130 of the sealable member 106.

Figure 4A:
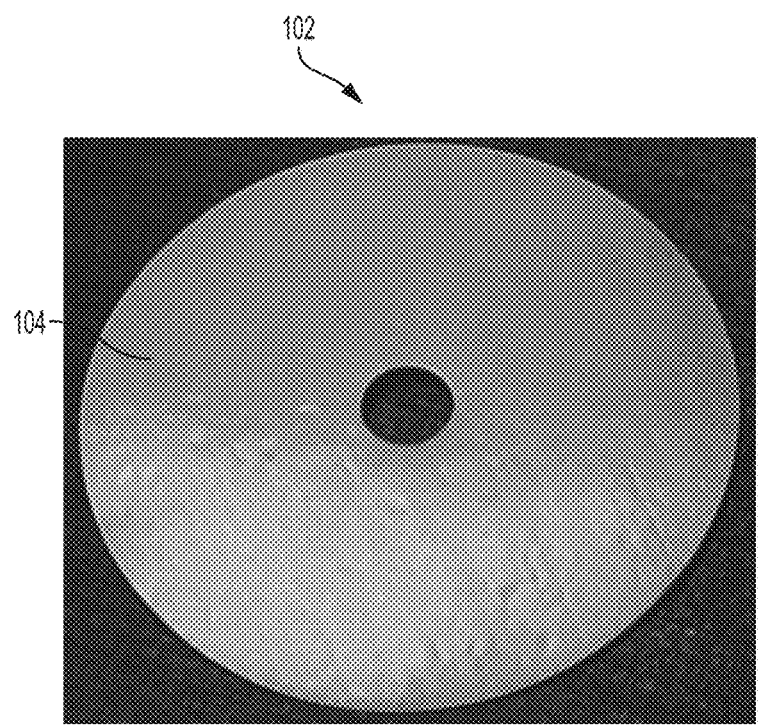
FIG. 4A is an image of the extruded side of the sealable member.

FIG. 4A is an image of the extruded side 104 of an exemplary sealable member. This sealable member has a diameter of 16 mm. The extruded side of the substrate 104 is about 0.1 mm thick.

Figure 4B:
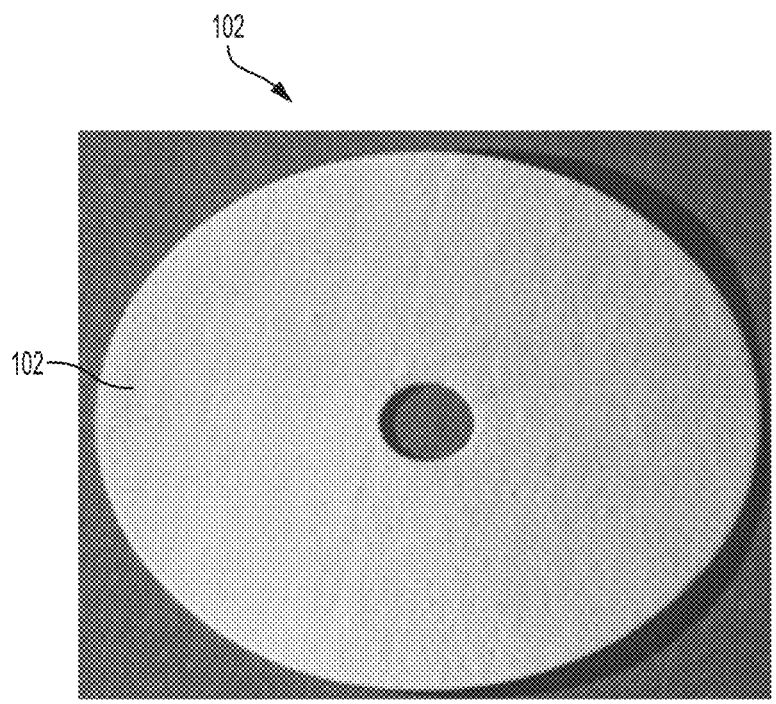
FIG. 4B is an image of the electrospun side of the sealable member.

FIG. 4B is an image of the electrospun side 102 of the sealable member 106. The electrospun side of the mesh layer 102 is about 0.02 mm thick.

Figure 5:
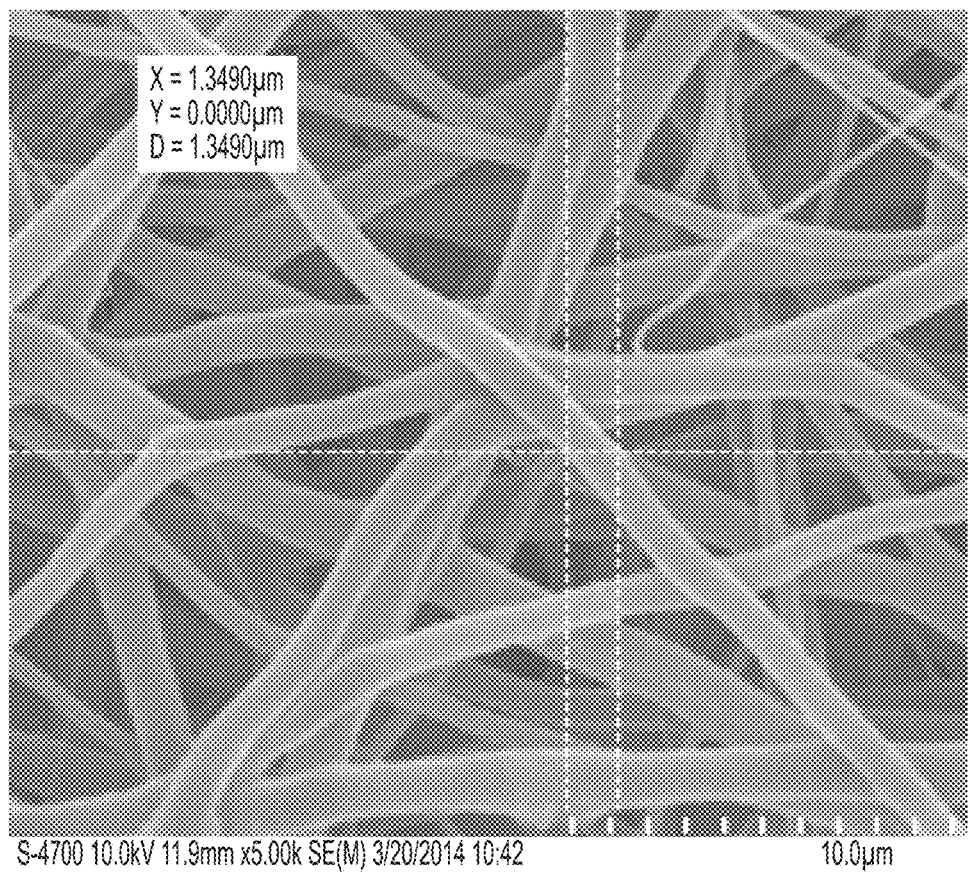
FIG. 5 is a SEM image of the electrospun side of the sealable member under magnification.

FIG. 5 is a SEM image of the electrospun side 102 under magnification. The fibers of the mesh layer have diameters in the range between about 0.1 µm and 8 µm.

In some embodiments, the systems, devices, and methods may be used for closing a surgical perforation in, and/or repairing, smaller blood vessels (e.g., small arteries and small veins). The dimensions of devices may be adjusted to be delivered in the smaller blood vessels.

EXAMPLE 1

Closure of Holes in Blood-Carrying Vessels

In certain embodiments, the flexible wing 106 is designed to seal the arteriotomy when positioned juxtaposed to the artery lumen 110. The flexible bilayer wing 106 is delivered into the vessel 100 in a folded or constricted state. Once in the vessel 110, the flexible wing 106 is positioned at the arteriotomy with the electrospun surface 102 next to the vessel lumen 110, where it regains its original structure forming a seal.

Figure 6:
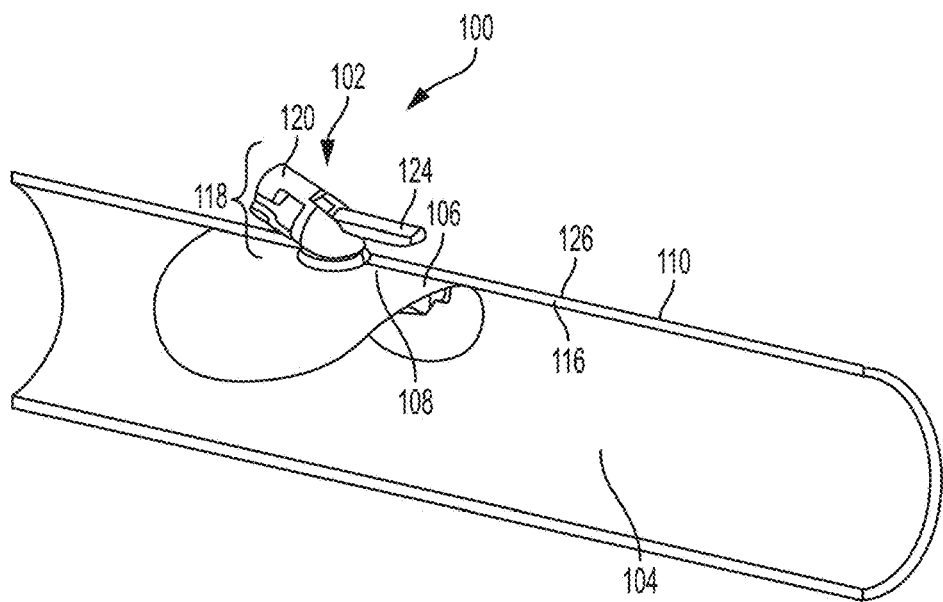
FIGS. 6, 7A and 7B are diagrams of an exemplary closure device deployed at an arteriotomy.
Figure 7A:
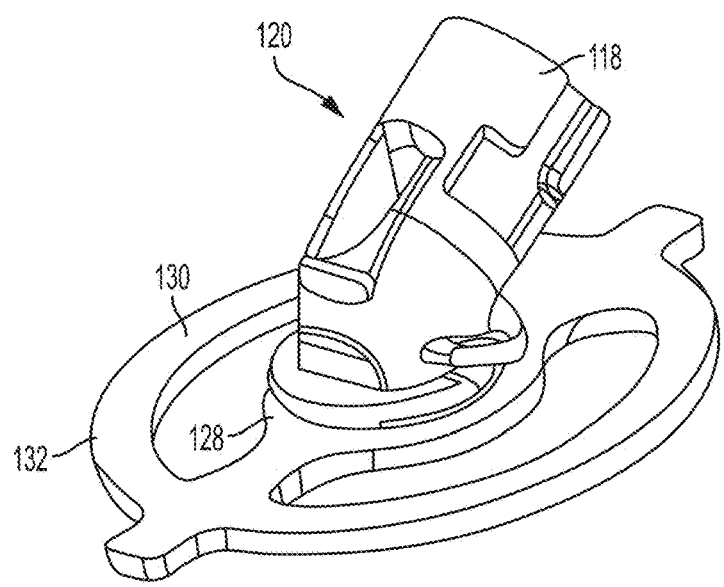
Figure 7B:
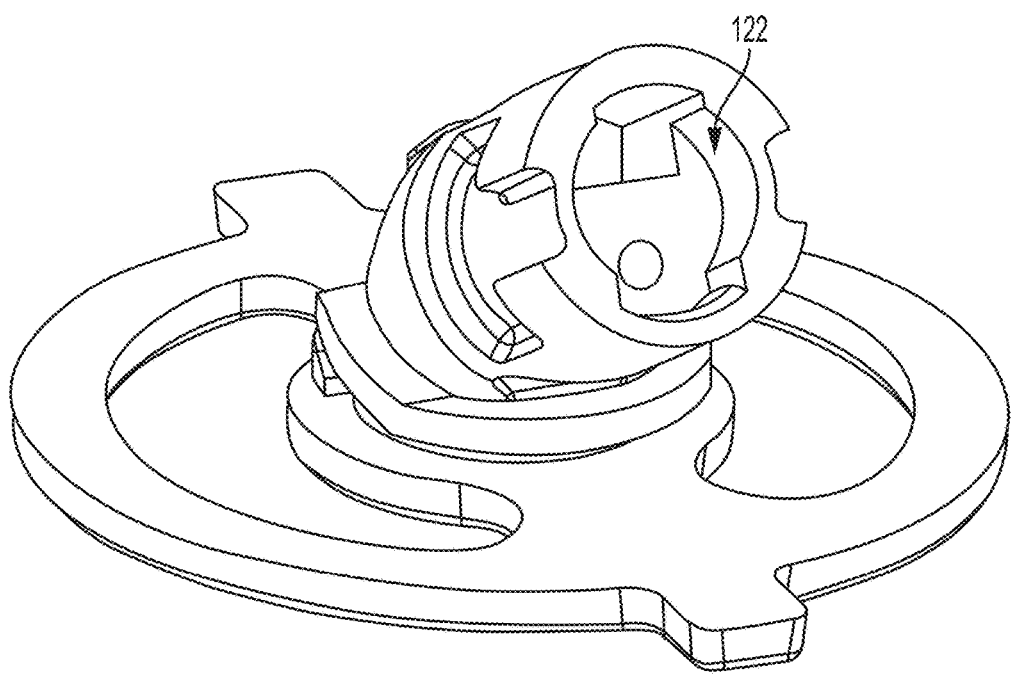

FIGS. 6, 7A and 7B are diagrams of an exemplary closure device 100 deployed at an arteriotomy. As shown in FIG. 6, the closure device 100 includes the sealable member 106 (e.g., a flexible wing) positionable against an interior surface 116 of the tissue 110 adjacent the aperture 108 in the tissue (e.g., so as to form a tamponade at the aperture 108). FIG. 7A is a diagram of an exemplary anchorable member 120. The anchorable member 120 includes a flexible base 132 having a central portion 128 and lateral portions 130 extending outwardly.

Although flat or slightly curved when in a relaxed state, the sealable member 106 flexibly curves to conform to the interior surface 108 of the lumen 112 to which it engages, in the deployed state (see FIG. 6). In such state, the flexible base 132 holds, in some embodiments, the sealable member 106 against the tissue 110. Examples of the anchorable members with a flexible base are described in U.S. Provisional Application Nos. 62/092,235 and 62/092,240, titled "Closure Apparatus with Flexible Sealable Member and Flexible Support Member", the contents of which are incorporated by reference herein in their entirety.

In some embodiments, the column 118 of the anchorable member 120 has an engagement portion 122 (see FIG. 7B) to secure a guard member 124 (e.g., an insertable or engagable pin or cage) to the support member 120, thereby engaging the guard member 124 against the exterior surface 126 of the tissue 110 when the closure device 100 is in the sealing position. The guard member 124 is moveable, from a stowed state to a deployed state, to engage the exterior surface 126 of the tissue adjacent the aperture 108 such that a portion of the tissue is disposed between the guard member 124 and the sealable member 106 when the closure device 100 is in the sealing position. In certain embodiments, the engagement does not exert a force on the tissue, but merely provides a structure to keep the closure device 100 at its deployed location, e.g., whereby the device 100 is prevented from dislodgement from its deployed location. In certain embodiments, the guard member 124 is an extra-luminal pin. Examples of the extra-luminal pin are described in U.S. Patent Application Publication No. US 2014/0018847, titled "Percutaneous Perforation Closure Systems, Devices, and Methods."

In other embodiments, the engagement results in a force being applied on the tissue by the anchorable member 120 and the guard member 124.

The sealable member 106, in some embodiment, is sized to be larger than the diameter of the aperture, e.g., between 12 French (F) and 30 French (F). In some embodiments, the sealable member 106 is sized to be larger than the diameter of the aperture, e.g., between 6 French (F) and 18 French (F). The sealable member 106 is preferably circular in shape. It should be understood, however, that other geometries may be employed for the sealable member, including, but not limited to, ovals, and other elongate shapes.

The sealable member 106, in some embodiments, has a hole (e.g., located in the center of the sealable member 106) sized to accept the column 118. In some embodiments, the sealable member 106 is free to rotate relative to the base of the support member 120 about an axis concentric to the column 118. Other examples of the sealable member is described in U.S. Patent Application Publication No. US 2014/0018847, titled "Percutaneous Perforation Closure Systems, Devices, and Methods."

In some embodiments, during deployment to close a hole, e.g., in a hollow vessel, the implant 100 is loaded into a delivery cannula through a loading funnel which reduces the cross-sectional area of the implant 100 (e.g., support member 118 and sealable member 106) to make it possible to deliver the implant through the delivery cannula into the hollow vessel (such as an artery or a vein).

Figure 8:
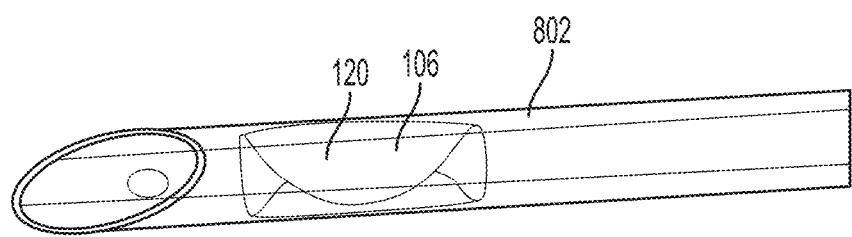
FIG. 8 is a diagram of the sealable member comprising the mesh layer and substrate folded in a delivery cannula of a closure device delivery system.

FIG. 8 is a diagram of the sealable member 106 comprising the mesh layer 102 and substrate 104 folded in a delivery cannula 802 of a closure-device delivery system. As shown, the sealable member is folded and assembled onto the closure device, which is connected to a shaft of the delivery system. Both the sealable member 106 and the support member 120 are folded into their delivery state. The support member 120 is positioned, in some embodiments, within the delivery cannula 802 such that it is surrounded by the sealable member 106. In some embodiments, the electrospun layer 102 is oriented to be facing the wall of the delivery cannula 802 such that the substrate layer 104 faces the center of the delivery cannula 802.

Figure 9A:
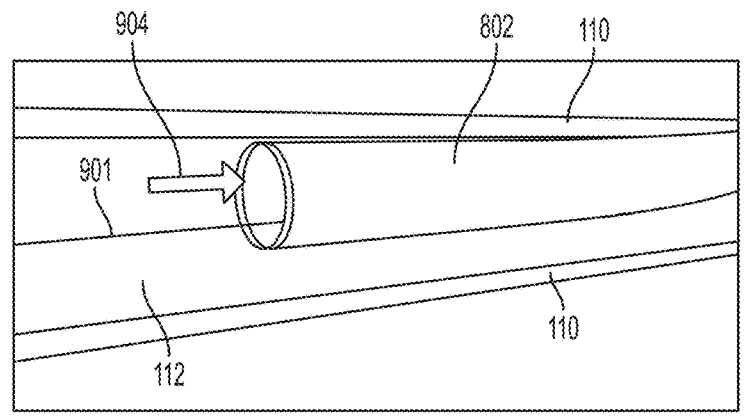
FIG. 9A is a diagram of the sealable member, in the delivery state, being introduced into a vessel.

FIG. 9A is a diagram of the sealable member, in the delivery state, being introduced into a vessel 110. A guide wire 901 may be employed to guide the delivery cannula 802 through the tissue 110 and into the lumen 112. To deploy the sealable member 106 in the lumen 112, the cannula 802 is translated back (see arrow 904), in some embodiments, by a mechanical actuation of the delivery system, while the sealable member 106 remains generally stationary with respect to the lumen 112. Consequently, the delivery cannula 802 passes the sealable member 106, whereby the sealable member 106 then unfolds.

Figure 9B:
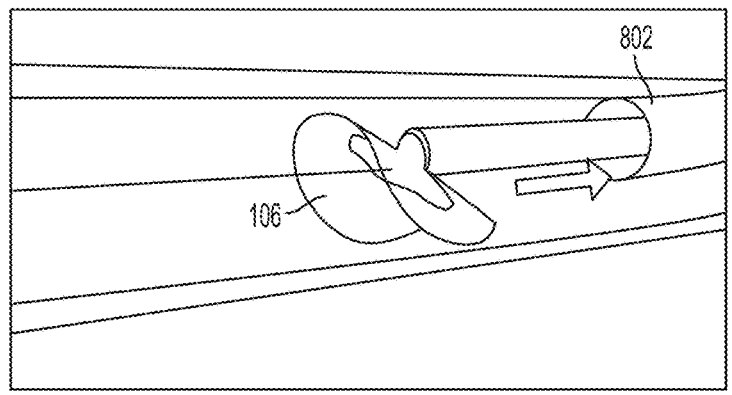
FIG. 9B is a diagram of the sealable member, in the deployed state, being deployed in the vessel.

FIG. 9B is a diagram of the sealable member, in the deployed state, being deployed in the vessel 112. As shown, the sealable member 106 has unfolded to a deployed state in the lumen 112. In some embodiments, the support member 120 also unfolds with the sealable member 106 (not shown). The sealable member 106 is now ready to be positioned against the aperture (e.g., the puncture site) in the body lumen.

Figure 9C:
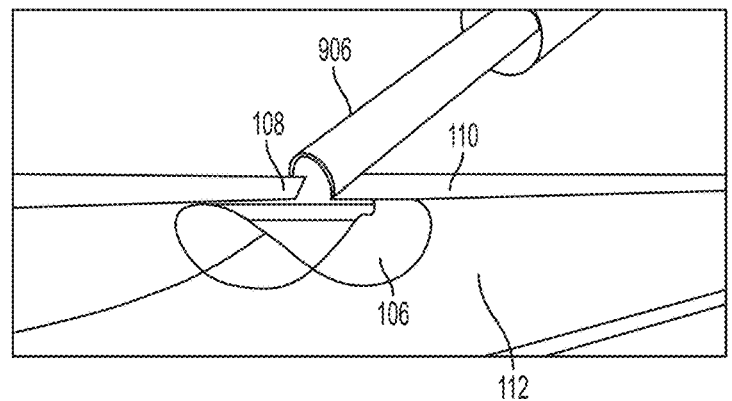
FIG. 9C is a diagram of the sealable member being positioned, at the sealing position.

FIG. 9C is a diagram of the sealable member being positioned, at the sealing position. As shown, the sealable member 106 has been withdrawn from the point of insertion such that the sealable member 106 now contacts the tissue 110 of the lumen 112. The sealable member 106 is positioned over the aperture 108 and is then released from the delivery shaft 906. In some embodiments, a guard member (e.g., an extra-luminal pin or slotted cage) is deployed from the delivery system to engage the closure device 100 (see, for example, FIG. 6) so as to secure and/or hold the closure device 100 in the sealing position and, e.g., prevent the inadvertent dislodgement of the device 100 from its sealing position, e.g., due to application of external forces.

EXAMPLE 2

Fabrication of the Material System Comprising a Mesh Layer and Substrate

Figure 12:
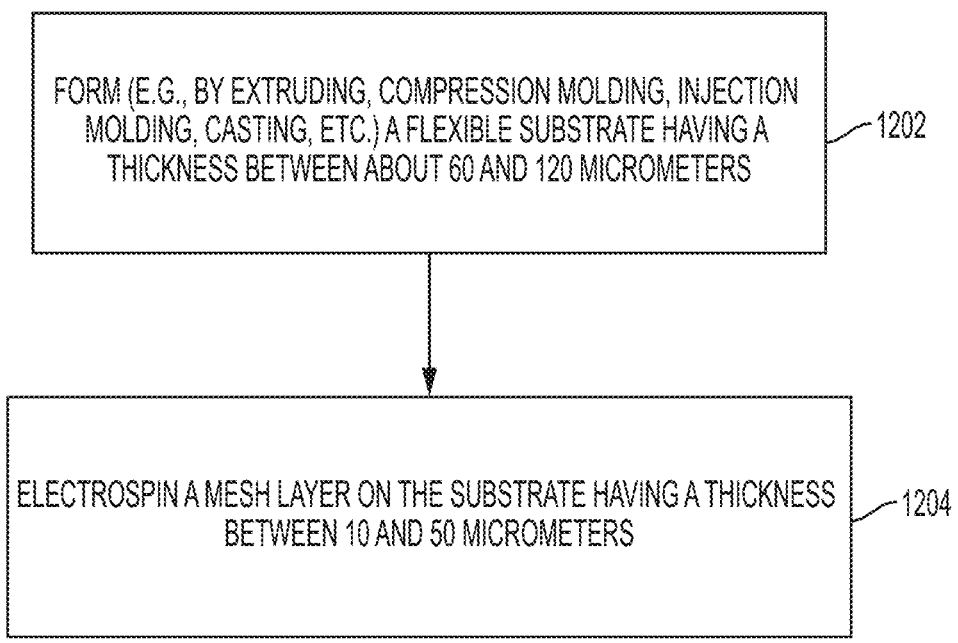
FIG. 12 is a diagram of a process for fabricating the material system comprising a mesh layer and a substrate, forming a sealable member, according to illustrative embodiments.

FIG. 12 is a diagram of a process for fabricating a material system comprising a mesh layer and a substrate, forming a sealable member, according to illustrative embodiments.

The method includes forming (e.g., by an extrusion process, a molding process (e.g., compression molding, injection molding, etc.), or a casting process) a flexible substrate 104 (1202). In some embodiments, the substrate-forming process produces a flexible substrate layer 104 having a thickness in a range from about 60 µm to about 120 µm. The substrate 104 can flexibly bend, in some embodiments, such that opposing ends of the substrate can overlap when under load and to return to an original shape of the substrate when the load is removed. In some embodiments, the forming process produces a thickness (of the substrate) between about 40 µm and about 500 µm, or between about 40 µm and about 750 µm, or between about 40 µm and about 1000 µm, or between about 40 µm and about 1500 µm, or between about 40 µm and about 2,000 µm, or between about 40 µm and about 2500 µm, or between about 40 µm and about 3000 µm, or between about 40 µm and about 4000 µm.

The method then includes forming (e.g., by an electrospun process) a mesh layer 102 on the substrate 104 (1204) In certain embodiments, the electrospinning produces a mesh layer 102 having a thickness in a range from about 10 µm to about 50 µm. A majority of the fibers of the mesh layer (e.g., greater than 50%, greater than 80%, or greater than 90%) has diameter in a range from about 0.3 µm to about 8 µm.

In some embodiments, the electrospun process produces a mesh layer having a thickness between about 5 µm and about 500 µm, or between about 5 µm and about 750 µm, or between about 5 µm and about 1000 µm, or between about 5 µm and about 1500 µm, or between about 5 µm and about 2000 µm, or between about 5 µm and about 2500 µm, or between about 5 µm and about 3000 µm, or between about 5 µm and about 4000 µm.

In some embodiments, the mesh layer is substantially formed (e.g., greater than 50%) with fibers structured (e.g., sized and shaped) to promote platelet capture (e.g., whereby the captured platelets encourages localized platelet activation, e.g., when in contact with collagen from the exposed wound, at the wound surfaces) when the device is in the sealing position.

Some embodiments of the present invention are directed to a closure system, device, and method of percutaneous closure of an arteriotomy following endovascular/intra S arterial procedures.

Some embodiments of the present invention are directed to a closure system, device, and method of percutaneous closure of an arteriotomy following endovascular/intra S arterial procedures.

With regards to the arterial wall morphology, in the context of example embodiments directed to closing arterial perforations, the fibrous adventitial layer of an artery (i.e., the outer layer) is relatively tough, whilst the intimal and medial/endothelial layers are friable. Because of the morphology of the arterial wall, an arteriotomy may be circumferential in nature and perpendicular to the longitudinal axis of the artery.

One of ordinary skill in the art will recognize that many mammalian lumina are comprised of one or more friable tissues. Thus, a common difficulty associated with surgical closure of a perforation in such lumina is that suture material, used in typical closure systems, tends to cause tears in the friable tissue. Such tearing of the luminal tissue impedes healing and causes scarring. Indeed, such tearing of the friable tissues of the interior lumina of blood vessels can lead to scarring, dislodgment of tissue particles, blockage, or even eventual death of the patient. In view of the fragile nature of luminal tissues, an aspect of example embodiments of the present invention is to provide systems, devices, and methods that allow a seal to be formed over a closure of a tissue perforation in a reliable manner with minimal trauma to the luminal tissue, for example, by providing a sutureless seal.

In certain embodiments, the invention is used for closing access site holes from abdominal post endoscopic procedures.

In certain embodiments, the fibers of the mesh layer are impregnated and/or coated with one or more therapeutic agents. Such therapeutic agents may include drugs, e.g., antibiotics (e.g., to control infection), anti-proliferative(s) (e.g., for hyperplasia), among others. In other embodiments, the one or more therapeutic agents may be impregnated within the structure of the mesh layer. Alternatively, or in conjunction with the mesh layer, the substrate layer may be impregnated and/or coated with the one or more therapeutic agents.

Experimental Data

The provided technologies were tested in vitro and in vivo. For the in vitro test, the sealable member was tested on a test bench using either a flexible tube or a bovine artery to simulate the body lumen. The bovine artery has an inner diameter between 7.8 mm and 9 mm and a wall thickness between 1.4 and 1.9 mm. The flexible tube has an inner diameter of 7.1 mm and a wall thickness of 0.55 mm. In each of the flexible tube and the bovine artery, an aperture was created with a diameter of 6-8 mm. A deployment sheath (e.g., the delivery cannula), used in the procedure, has an inner/outer diameter of 20 F/24 F.

The test was performed with water flowing through each of the respective bovine artery and flexible tube, under physiological conditions with a pulse of approximately 60 hertz, a systolic pressure of about 120 mm-Hg, and a diastolic pressure of about 80 mm-Hg. Ten data samples were collected for each test. The amount of water leaked within 5 minutes from the time of deployment is measured and provided in Table 4 and Table 5 below.

TABLE 4

Figure 10A:
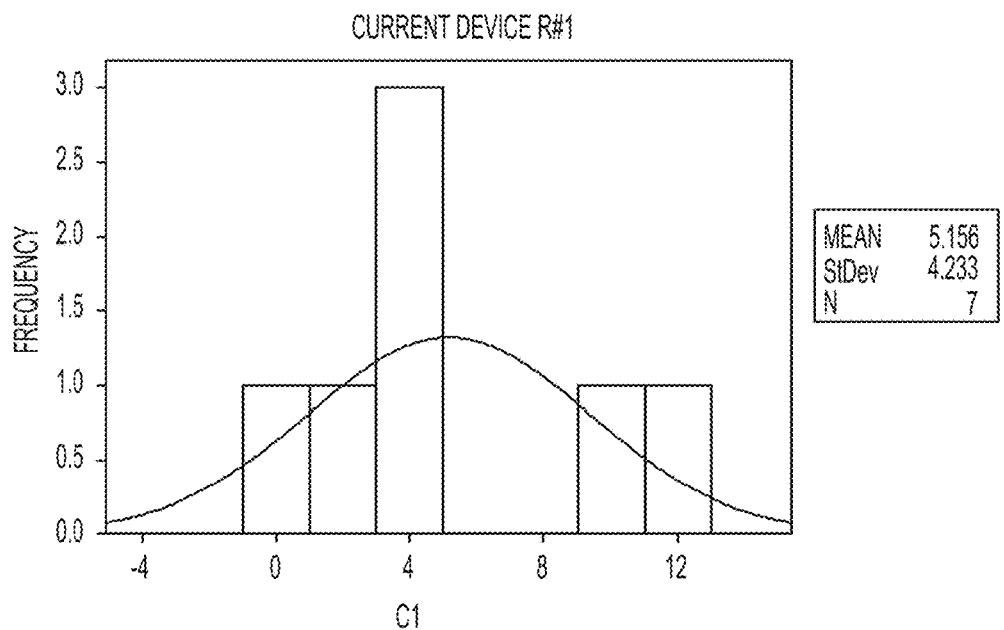
FIGS. 10A and 10B illustrate direct comparison of histograms of data used to generate Table 4. The data are of an in vitro leakage test on bovine artery, comparing (i) a baseline closure device having a rigid base core and a non-mesh sealable member and (ii) a closure device configured with a flexible support member and a sealable member comprising the mesh layer and substrate.
Figure 10B:
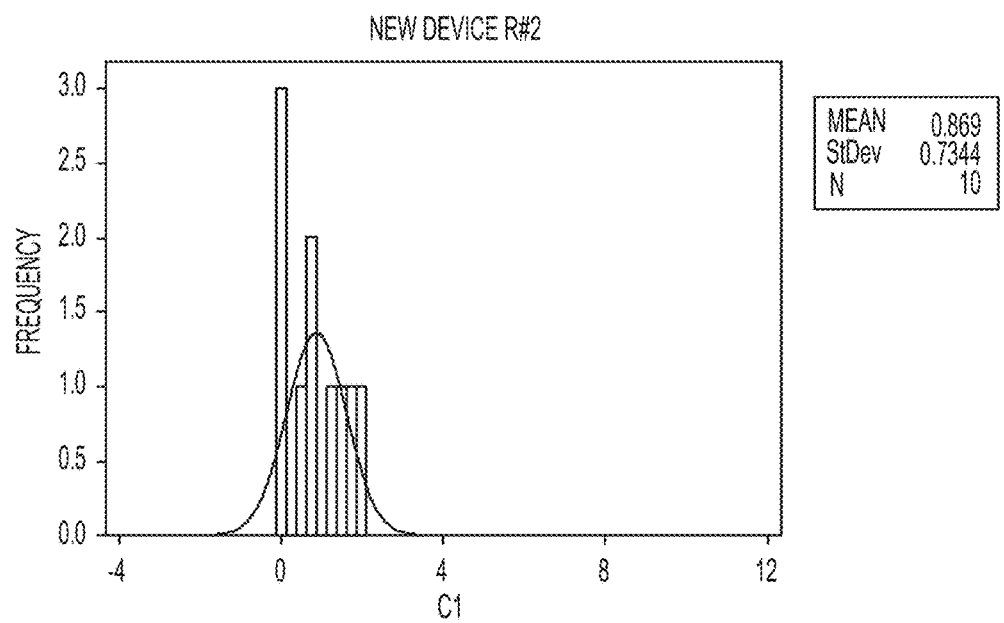

Bovine artery: in vitro test comparison of devices, including (i) a baseline closure device having a rigid base core and a non-mesh sealable member (see "Current Device R#1") and (ii) a closure device configured with an anchorable member comprising a flexible support base and a sealable member (comprising the mesh layer and substrate) (see "New Device R#2"). FIGS. 10A and 10B illustrate a direct comparison of histograms of data used to generate Table 4.

| Total leak in 5 ml (ml) | Current Device R#1 | New Device R#2 |
|---|---|---|
| Mean | 5.2 | 0.9 |
| SD | 4.2 | 0.7 |
| Min | 0.8 | 0.0 |
| Max | 12 | 2.0 |

TABLE 5

Figure 11A:
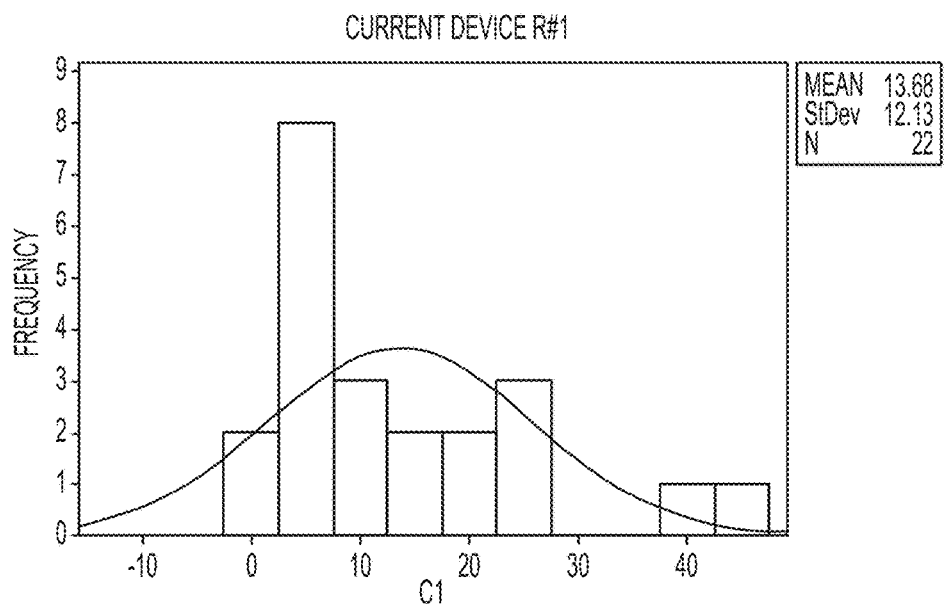
FIGS. 11A and 11B illustrate direct comparison of histograms of data used to generate Table 5. The data are of an in vitro leakage test on a flexible tube, comparing (i) a baseline closure device having a rigid base core and a non-mesh sealable member and (ii) a closure device configured with a flexible support member and a sealable member comprising the mesh layer and substrate.
Figure 11B:
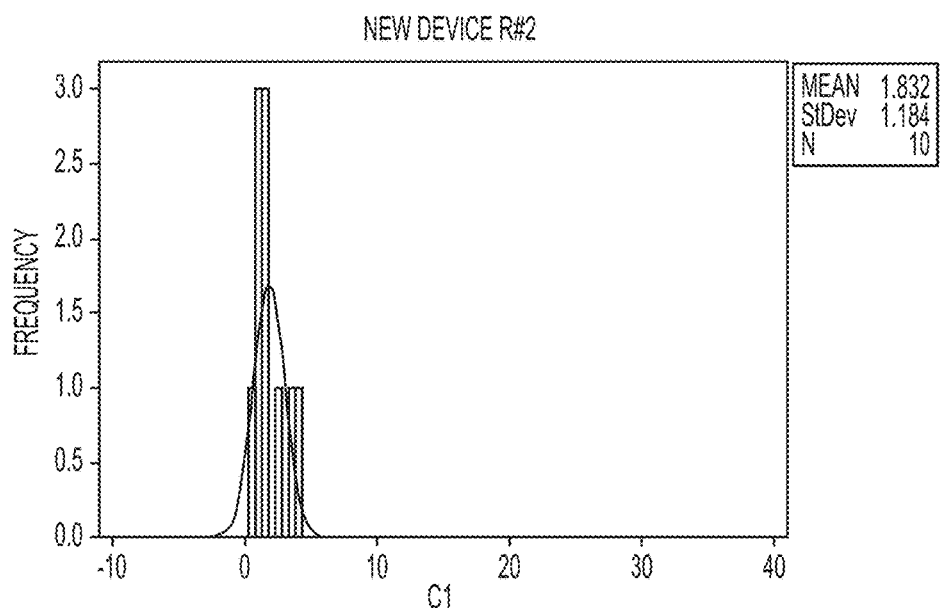

Flexible tube: in vitro test comparison of devices, including (i) the same baseline closure device having a rigid base core and a non-mesh sealable member (see "Current Device R#1") and (ii) the same closure device configured with an anchorable member comprising a flexible support base and a sealable member (comprising the mesh layer and substrate) (see "New Device R#2"). FIGS. 11A and 11B illustrate a direct comparison of histograms of data used to generate Table 5.

| Total leak in 5 ml (ml) | Current Device R#1 | New Device R#2 |
|---|---|---|
| Mean | 13.6 | 1.8 |
| SD | 12.0 | 1.2 |
| Min | 0 | 0.6 |
| Max | 16 | 4.1 |

The test illustrates a 5× improvement of the closure device, configured with a flexible support member and a sealable member comprising the mesh layer and substrate, in reducing the amount of fluid leakage over a current design employing a sealable with no mesh layer (and having a rigid core). In addition to the seal formed from the R#2 closure device having improved leakage performance, as shown in the plots of the histograms and the standard deviation values of the tables, a more consistent closure is also provided.

For the in vivo test, the sealable member was tested in animal subjects. A similar 6 mm puncture was made in a pig aorta. The deployment sheath, used in the procedure, also has an inner/outer diameter of 20 F/24 F. Six data samples were collected for each test using the R#1 design and the R#2 design. The total deployment time, tamponade time, time to hemostasis, and total procedure time are provided in Table 6 below.

TABLE 6

Pig Aorta: in vivo study comparison of devices, including (i) the same baseline closure device having a rigid base core and a non-mesh sealable member (see "R#1") and (ii) the same closure device configured with an anchorable member with flexible support base and a sealable member (comprising the mesh layer and substrate) (see "R#2").

R#1 in vivo study

| n = 6 | Deployment Time (mm:ss) (Inc TT) | Tamponade Time (TT) (mm:ss) | Time to Hemostasis (TTH) (mm:ss) | Total Procedure Time (mm:ss) | ACT (sec) |
|---|---|---|---|---|---|
| Average | 07:01 | 04:08 | 05:49 | 12:50 | 190 |
| Max | 07:45 | 04:30 | 30:15 | 37:38 | 217 |
| Min | 06:24 | 04:00 | 00:00 | 07:00 | 165 |

R#2 in vivo study

| n = 6 | Deployment Time (mm:ss) (Inc TT) | Tamponade Time (TT) (mm:ss) | Time to Hemostasis (TTH) (mm:ss) | Total Procedure Time (mm:ss) | ACT (sec.) |
|---|---|---|---|---|---|
| Average | 02:50 | 00:57 | 00:38 | 03:29 | 294 |
| Max | 03:07 | 01:37 | 01:30 | 04:30 | 404 |
| Min | 02:15 | 00:20 | 00:00 | 02:15 | 194 |

As shown in Table 6, the R#2 design improves the total deployment time by 2.5× over the R#1 design. The total deployment time, used in the observations, includes the time for the device to be positioned and deployed in the pig aorta and for the leakage to stop.

In addition, the R#2 design improves the time to hemostasis by 9× over the R#1 design. The time to hemostasis (TTH), used in the observations, refers to the time from which a seal is created and the time for leakage to stop. Less variability in the time to hemostasis is also observed.

In addition, the R#2 design reduces the overall closure procedure time by 3.7× over the R#1 design. The activated clotting time (ACT time) was longer by over 100 seconds. The activated clotting time refers to the time for whole blood to clot upon exposure to an activator.

Although certain figures and embodiments relate to use of systems and devices for closure of a perforation associated with vascular surgery, one of ordinary skill in the art will appreciate that components of a provided device are not size dependent (i.e., are scalable) and are therefore useful for closure of any perforation in a lumen of a mammal.

Although the present invention has been described with reference to particular examples and exemplary embodiments, it should be understood that the foregoing description is in no manner limiting. Moreover, the features described herein may be used in any combination.

What is claimed is:

1. An implantable device system for sealing an aperture in a tissue of a body lumen, the implantable device system comprising:
   a sealable member, comprising a flexible substrate and a mesh layer deposited on the flexible substrate, wherein, when the implantable device is in a sealing position, the sealable member is disposed against an internal surface of the tissue adjacent the aperture such that the mesh layer is in contact with the internal surface, wherein the mesh layer comprises a plurality of electrospun fibers, and wherein the mesh layer facilitates tissue adhesion to the sealable member by promoting platelet aggregation in the sealing position; and a delivery tube containing the sealable member in a rolled conformation therein, wherein each of the plurality of electrospun fibers has a diameter in a range from 0.3 μm to 8 μm, wherein the plurality of electrospun fibers makes up from 1% to 35% of the mesh layer by volume, and wherein, when the sealable member is in the sealing position, at least one dimension of the sealable member is larger than a cross-sectional area of a 6 French aperture.

2. The implantable device system of claim 1, wherein the mesh layer comprises at least one material selected from the group consisting of polydioxanone, poly-L-lactide, poly-D-lactide, poly-DL-lactide, polyglycolide, ε-caprolactone, polyethylene glycol, and a copolymer thereof.

3. The implantable device system of claim 1, wherein the flexible substrate comprises at least one material selected from the group consisting of polydioxanone, poly-L-lactide, poly-D-lactide, poly-DL-lactide, polyglycolide, ε-caprolactone, polyethylene glycol, and a copolymer thereof.

4. The implantable device system of claim 1, wherein the mesh layer and/or the flexible substrate comprise polydioxanone.

5. The implantable device system of claim 1, wherein the mesh layer is made of a material different from the material of the flexible substrate.

6. The implantable device system of claim 1, wherein the plurality of electrospun fibers makes up from 5% to 25% of the mesh layer by volume.

7. The implantable device system of claim 1, wherein a substantial portion of the electrospun fibers has a random orientation.

8. The implantable device system of claim 1, wherein a substantial portion of the electrospun fibers has a patterned orientation.

9. The implantable device system of claim 1, wherein the sealable member is sized to seal an arteriotomy of an arterial lumen.

10. The implantable device system of claim 9, wherein the arterial lumen is selected from the group consisting of a femoral artery, an iliac artery, a subclavian artery, an ascending aorta, a descending aorta, an auxiliary artery, and a brachial artery.

11. The implantable device system of claim 1, wherein the sealable member is sized to close a perforation in a vein.

12. The implantable device system of claim 11, wherein the vein is selected from the group consisting of a femoral vein, an iliac vein, a subclavian vein, and a vena cava.

13. The implantable device system of claim 1, wherein the sealable member is sized to close a perforation in a member selected from the group consisting of a gastrointestinal tract, a heart, a peritoneal cavity, an esophagus, a vagina, a rectum, a trachea, and bronchi.

14. The implantable device system of claim 1, wherein the mesh layer has a first thickness, and the flexible substrate has a second thickness, wherein the second thickness is greater than the first thickness.

15. The implantable device system of claim 14, wherein the first thickness is between about 10 and 50 μm.

16. The implantable device system of claim 14, wherein the second thickness is between about 60 and 120 μm.

17. The implantable device system of claim 1, wherein the mesh layer has a first thickness, and the first thickness is between about 100 and 1000 μm.

18. The implantable device system of claim 1, wherein the flexible substrate has a second thickness, and the second thickness is between about 20 and 100 μm.

19. The implant device system of claim 1, further comprising an anchorable member positionable against the sealable member to retain the sealable member at the sealing position.

20. The implant device system of claim 1, wherein, when the sealable member in the rolled conformation, the sealable member has cross-sectional area smaller than a cross-sectional area of a 30 French aperture.

21. An implantable device for sealing an aperture in a tissue of a body lumen, the implantable device comprising:
a sealable member
comprising a flexible substrate and a mesh layer deposited on the flexible substrate,
wherein, when the implantable device is in a sealing position, the sealable member is disposed against an internal surface of the tissue adjacent the aperture such that the mesh layer is in contact with the internal surface,
wherein the mesh layer comprises a plurality of electrospun fibers,
wherein the mesh layer facilitates tissue adhesion to the sealable member by promoting platelet aggregation in the sealing position,
wherein, when the implantable device is in a delivery configuration, the sealable member is rolled, so that a delivery cross-sectional area of the rolled sealable member is smaller than a cross-sectional area of a 30 French aperture,
wherein each of the plurality of electrospun fibers has a diameter in a range from 0.3 μm to 8 μm, and
wherein the plurality of electrospun fibers makes up from 1% to 35% of the mesh layer by volume.

22. The implantable device of claim 21, wherein, when the implantable device is in the sealing position, at least one dimension of the sealable member is larger than a cross-sectional area of a 6 French aperture.

23. An implantable device for sealing an aperture in a tissue of a body lumen, the implantable device comprising:
a sealable member
comprising a flexible substrate and a mesh layer deposited on the flexible substrate,
wherein, when the implantable device is in a sealing position, the sealable member is disposed against an internal surface of the tissue adjacent the aperture such that the mesh layer is in contact with the internal surface,
wherein the mesh layer comprises a plurality of electrospun fibers,
wherein the mesh layer facilitates tissue adhesion to the sealable member by promoting platelet aggregation in the sealing position,
wherein, when the implantable device is in the sealing position, at least one dimension of the sealable member is larger than a cross-sectional area of a 6 French aperture,
wherein each of the plurality of electrospun fibers has a diameter in a range from 0.3 μm to 8 μm, and
wherein the plurality of electrospun fibers makes up from 1% to 35% of the mesh layer by volume.

* * * * *